US008178292B2

(12) United States Patent
Yokota

(10) Patent No.: US 8,178,292 B2
(45) **Date of Patent: *May 15, 2012**

(54) METHODS OF DIAGNOSING ACUTE MYELOID LEUKEMIA USING NUCLEIC ACIDS ENCODING FLT3 KINASE

(75) Inventor: Shohei Yokota, Kyoto (JP)

(73) Assignee: Takara Bio Inc., Otsu-shi (JP)

( * ) Notice: Subject to any disclaimer, the term of this patent is extended or adjusted under 35 U.S.C. 154(b) by 400 days.

This patent is subject to a terminal disclaimer.

(21) Appl. No.: 11/892,241

(22) Filed: Aug. 21, 2007

(65) Prior Publication Data

US 2008/0241173 A1 Oct. 2, 2008

Related U.S. Application Data

(62) Division of application No. 10/653,147, filed on Sep. 3, 2003, now abandoned, which is a division of application No. 09/942,711, filed on Aug. 31, 2001, now Pat. No. 6,846,630, which is a division of application No. 09/284,654, filed as application No. PCT/JP97/03667 on Oct. 13, 1997, now abandoned.

(30) Foreign Application Priority Data

Oct. 18, 1996 (JP) ...................................... 8-297329

(51) Int. Cl.
*C12Q 1/68* (2006.01)
*C07H 21/04* (2006.01)

(52) U.S. Cl. .......................................... 435/6; 536/23.1

(58) Field of Classification Search ........................ None
See application file for complete search history.

(56) References Cited

U.S. PATENT DOCUMENTS 5,270,458 A 12/1993 Lemischka
5,618,709 A 4/1997 Gewirtz et al.
6,846,630 B2 * 1/2005 Yokota ............................. 435/6

FOREIGN PATENT DOCUMENTS

WO WO-95-00554 A 1/1995
WO WO-95-19175 A 7/1995

OTHER PUBLICATIONS

Database BIOSIS on DIALOG, BIOSIS No. 99755642, S. Horike et al., abstract.
Leukemia (Basingstroke) 11(9), pp. 1442-1446 (1997).
Database BIOSIS on DIALOG, BIOSIS No. 99364760, M. Nanao et al., abstract, Leukemia (Basingstoke) 10(12), pp. 1911-1918 (1996).
Rosnet et al., Blood, 84, pp. 1110-1119 (1993).
D. Small et al., Proc. Natl. Acad. Sci. USA, 91, pp. 459-463 (1994).
W. Matthews et al., Cell., 65, pp. 1143-1152 (1991).
Michael Rossner et al., "Fms-like tyrosine kinase 3 catalytic domain can transduce a proliferative signal in FDC-P1 cells that is qualitatively similar to the signal delivered by c-Fms", Cell Growth and Differentiation, vol. 5, No. 5, 1994, pp. 549-555, XP001105308.
Francis Zeigler et al., "Cellular ad molecular characterization of the role of the FLK-2/FLT-3 receptor tyrosine kinase in hematopoietic stem cells", Blood, vol. 84, No. 8, 1994, pp. 2422-2430, XP002212829.
Birg et al., (Blood, 1992, 80:2584-2593).
Panagiotis et al., (Blood, 2002, 100:2393-2398).
Office Action dated Sep. 16, 2010 for U.S. Appl. No. 12/557,193.

* cited by examiner

*Primary Examiner* — Ruixiang Li
(74) *Attorney, Agent, or Firm* — Birch, Stewart, Kolasch & Birch, LLP

(57) ABSTRACT

To provide a nucleic acid encoding a receptor protein kinase, wherein the nucleic acid has tandem duplication in a nucleotide sequence of a juxtamembrane and is useful for diagnosis of leukemia; a polypeptide encoded by the nucleic acid; an antibody capable of specifically binding to a region encoded by the nucleic acid having tandem duplication occurring in a nucleotide sequence of a juxtamembrane; a nucleic acid capable of specifically binding to the nucleic acid having tandem duplication occurring in a nucleotide sequence of a juxtamembrane; a method for detection of the nucleic acid encoding a receptor protein kinase; and a kit therefor. A nucleic acid encoding a receptor protein kinase, wherein the nucleic acid has tandem duplication in a nucleotide sequence of a juxtamembrane; a polypeptide encoded by the nucleic acid; an antibody capable of specifically binding to the portion of the polypeptide; a nucleic acid capable of specifically binding to the nucleic acid; a method for detection of the nucleic acid; and a kit for detection.

3 Claims, 2 Drawing Sheets

METHODS OF DIAGNOSING ACUTE MYELOID LEUKEMIA USING NUCLEIC ACIDS ENCODING FLT3 KINASE

This application is a Divisional of application Ser. No. 10/653,147, filed on Sep. 3, 2003 now abandoned, the entire contents of which are hereby incorporated by reference and for which priority is claimed under 35 U.S.C. §120. Application Ser. No. 10/653,147 is a divisional of application Ser. No. 09/942,711 filed on Aug. 31, 2001, issued as U.S. Pat. No. 6,846,630 on Jan. 25, 2005, which is a divisional of abandoned application Ser. No. 09/284,654 filed on Apr. 16, 1999 and for which priority is claimed under 35 U.S.C. §120. Application Ser. No. 09/284,654 is the national phase of PCT International Application No. PCT/JP97/03667 filed on Oct. 13, 1997 under 35 U.S.C. §371. The entire contents of each of the above-identified applications are hereby incorporated by reference. This application also claims priority of Application No. 8-297329 filed in Japan on Oct. 18, 1996 under 35 U.S.C. § 119.

TECHNICAL FIELD

The present invention concerns a nucleic acid encoding a receptor protein kinase, which has tandem duplication in a nucleotide sequence of a juxtamembrane, a polypeptide, a method for detection of the above nucleic acid and a kit for detection.

BACKGROUND ART

Proliferation and differentiation of cells, and responses of cells to various stimuli are strictly regulated by various growth factors. These growth factors are known to act via receptors which are specific to the above growth factors (Nicola, N. A., *Annu. Rev. Biochem.* 58, 45, 1989; Lowenberg, B., Blood 81, 281, 1991). Of those receptors, the receptors containing a tyrosine kinase domain are classified as receptor tyrosine kinases (RTKs).

RTKs comprise an entracellular region, a transmembrane region, as well as an intracellular region containing a tyrosine kinase domain and a juxtamembrane between the transmembrane region and the tyrosine kinase domain, and further roughly classified into four types according to structural characteristics and amino acid sequence homology.

Type I receptors have a monomeric structure, with two cysteine-rich repeat sequences in their extracellular region, and are exemplified by the EGF receptor, HER2/neu and the like.

Type II receptors have a structure comprising two subunits each for $\alpha$ and $\beta$, which are bound via S—S bond, wherein the $\alpha$ chain is an extracellular region containing one cysteine-rich repeat sequence, and wherein the $\beta$ chain has a transmembrane region, a juxtamembrane, and a tyrosine kinase domain. Examples are an insulin receptor and an IGF-1 receptor.

Type III receptors have a monomeric structure containing five immunoglobulin-like cysteine-rich sequences in their extracellular region and two tyrosine kinase domains interrupted by a kinase insert in their intracellular region. Examples are PDGF receptor, fms (CSF-1 receptor), kit (SLF receptor) and the like.

Type IV receptors resemble type III receptors but have three immunoglobulin-like repeat sequences, and are exemplified by FGF receptor.

fms-Like tyrosine kinase 3 (hereinafter abbreviated as FLT3; Matthews, W., *Cell* 65, 1143, 1991; Rosnet, O., *Genomics* 9, 380, 1991), which is expressed in leukemic cells etc., also referred to as fetal liver kinase 2 (FLK2) or STK-1, is known to as type III receptors (Small, D., *Proc. Natl. Acad. Sci. USA* 91, 459, 1993; Lyman, S. D., *Oncogene* 8, 815, 1993; Rosnet, O., *Blood* 82, 1110, 1993; Agnes, F., *Gene* 145, 283, 1994).

In these receptor tyrosine kinases, aggregation, such as dimerization, takes place upon binding of a ligand, such as a growth factor, to the extracellular region, thereby resulting in the activation of kinase. Although in these tyrosine kinases, their ligands have been first found and then their receptors in most cases, there are receptors of which ligands remain unknown.

Regarding FLT3, which has been remarked in proliferation mechanism of hematopoietic stem cells and leukemia, after finding the FLT3, the FLT3 ligand has been found (Lyman, S. D., *Cell* 75, 1157, 1993; Hannum, C., *Nature* 368, 643, 1994). Since the FLT3 ligand is expressed in almost all leukemic cells, it is assumed that cells are proliferated by a mechanism of autocrine stimulation in leukemia (Meierhoff, G., *Leukemia* 9, 1368, 1995). Also, FLT3 mRNA has been reported to be expressed in lymphatic leukemic cells and myelocytic leukemic cells (Birg, F., *Blood* 80, 2584, 1994; Da Silva, N., *Leukemia* 8, 885, 1994; Brasel, K., *Leukemia* 9, 1212, 1995; Drexler, H. G., *Leukemia* 10, 588, 1996). However, there remains unknown how the FLT3 mRNA expression is associated with the pathology of lymphatic leukemia and myelocytic leukemia.

A human FLT3 cDNA has been cloned, and a cDNA nucleotide sequence and the amino acid sequence of the FLT3 protein have been determined [O. Rosnet et al., *Blood,* 82(4), 1110-1119 (1993)]. The present situation, however, is that the structure and function of FLT during the hematopoietic stem cell differentiation and the malignant alterations to leukemic cells have not been analyzed well.

DISCLOSURE OF INVENTION

Accordingly, a first object of the present invention is to provide a nucleic acid encoding a receptor protein kinase, wherein the nucleic acid has tandem duplication in a nucleotide sequence of a juxtamembrane and is useful for diagnosis of leukemia, and to provide a nucleic acid encoding the above juxtamembrane. A second object of the present invention is to provide a polypeptide which is encoded by the above nucleic acid. A third object of the present invention is to provide an antibody capable of specifically binding to a portion encoded by a nucleic acid having tandem duplication occurring in a nucleotide sequence of a juxtamembrane. A fourth object of the present invention is to provide a nucleic acid capable of specifically binding to a nucleic acid having tandem duplication occurring in a nucleotide sequence of a juxtamembrane. A fifth object of the present invention is to provide a method for detection of the nucleic acid encoding a receptor protein kinase and a kit therefor.

Conventionally, as to the FLT3, the same receptor protein kinase is expressed, irrespective of kinds of cells and differentiation [O. Rosnet et al., *Blood,* 82(4), 1110-1119 (1993)]. As a result of the detailed investigation and intensive studies of the FLT3 expression in leukemic cells, however, the present inventors surprisingly have found a receptor protein kinase gene having novel tandem duplication in a juxtamembrane, and found that the above tandem duplication is somatic, and that the expression of FLT3 having the above tandem duplication is associated with leukemia malignancy and mal-consequence of prognosis, and the present invention has been completed thereby.

Accordingly, the gist of the present invention is as follows:

[1] a nucleic acid encoding a receptor protein kinase, wherein the nucleic acid has tandem duplication in a nucleotide sequence of a juxtamembrane;

[2] the nucleic acid according to item [1] above, wherein the receptor protein kinase is a receptor tyrosine kinase;

[3] the nucleic acid according to item. [2] above, wherein the receptor tyrosine kinase is FMS-like tyrosine kinase 3 (FLT3);

[4] the nucleic acid according to any one of items [1] to [3] above, wherein the nucleic acid comprises a nucleotide sequence encoding an amino acid sequence as shown by any one of SEQ ID NOs: 1 to 5 in Sequence Listing in a juxtamembrane;

[5] the nucleic acid according to any one of items [1] to [3] above, wherein the nucleic acid comprises a nucleotide sequence as shown by any one of SEQ ID NOs: 6 to 15 in Sequence Listing in a juxtamembrane;

[6] a nucleic acid encoding a tandem duplication mutant of FLT3 as shown by any one of SEQ ID NOs: 16 to 20. in Sequence Listing;

[7] a nucleic acid comprising a nucleotide sequence encoding a tandem duplication mutant as shown by any one of SEQ ID NOs: 21 to 25 in Sequence Listing, or a nucleic acid capable of hybridizing thereto under stringent conditions, wherein the nucleic acid has tandem duplication in a nucleotide sequence encoding a juxtamembrane;

[8] a nucleic acid having tandem duplication, wherein the nucleic acid encodes an amino acid sequence as shown by any one of SEQ ID NOs: 1 to 5 in Sequence Listing;

[9] a nucleic acid as shown by any one of SEQ ID NOs: 6 to 15 in Sequence Listing, or a nucleic acid capable of hybridizing thereto under stringent conditions, wherein the nucleic acid has tandem duplication;

[10] a polypeptide encoded by the nucleic acid according to any one of items [1] to [9] above;

[11] a polypeptide comprising an amino acid sequence as shown by any one of SEQ ID NOs: 1 to 5, and 16 to 20 in Sequence Listing;

[12] a polypeptide encoded by a nucleic acid having tandem duplication in a nucleotide sequence of a juxtamembrane, wherein the polypeptide results from at least one of deletion, substitution or addition of one or more amino acid residues in an amino acid sequence as shown by any one of SEQ ID NOs: 1 to 5, and 16 to 20;

[13] an antibody capable of specifically binding to a region encoded by a nucleic acid having tandem duplication occurring in a nucleotide sequence of a juxtamembrane of a receptor protein kinase;

[14] a nucleic acid capable of specifically binding to a nucleic acid having tandem duplication occurring in a nucleotide sequence of a juxtamembrane of a receptor protein kinase;

[15] a method for detection of a nucleic acid encoding receptor protein kinase and having tandem duplication occurring in a nucleotide sequence of a juxtamembrane, comprising:

step (a): preparing a human nucleic acid sample;

step (b): subjecting the nucleic acid sample obtained in step (a) to gene amplification reaction to provide a nucleic acid fragment obtained by amplifying a region having tandem duplication in a juxtamembrane which can be found in a nucleic acid encoding a receptor protein kinase; and step (c): examining the presence of tandem duplication for the nucleic acid fragment of step (b);

[16] the method for detection according to item [15] above, characterized in that the method is utilized in diagnosis of M2, M4, or M5 based on the FAB (French-American-British) classification of acute myeloid leukemia;

[17] a kit for detection of a nucleic acid encoding a receptor protein kinase and having tandem duplication in the nucleotide sequence of a juxtamembrane, characterized in that the kit comprises primers for amplifying a region having tandem duplication, wherein the region can be found in the receptor protein kinase gene;

[18] the kit according to item [17] above, characterized in that the kit is utilized in diagnosis of M2, M4, or M5 based on the FAB (French-American-British) classification of acute myeloid leukemia; and

[19] use of the nucleic acid according to any one of items [1] to [9] above for detection of a nucleic acid encoding a receptor protein kinase and having tandem duplication in a nucleotide sequence of a juxtamembrane.

BEST MODE FOR CARRYING OUT THE INVENTION

The present invention will be explained below.

The nucleic acid encoding a receptor protein kinase of the present invention has tandem duplication in a region encoding a juxtamembrane. The nucleic acid of the present invention encoding a protein kinase can be a nucleic acid encoding either tyrosine kinase or serine-threonine kinase. For diagnosis of leukemia, preferred are nucleic acids encoding a receptor protein kinase, and nucleic acids encoding FMS-like tyrosine kinase 3 (FLT3) are preferably used.

In the present invention, the juxtamembrane is present between the transmembrane region and the kinase domain of the receptor protein kinase, and the juxtamembrane constructs an intracellular membrane region together with the kinase domain [O. Rosnet, et al., *Blood,* 82 (4), 1110-1119 (1993)].

In the present invention, tandem duplication refers to a nucleotide sequence in which an entire portion or partial portion of a nucleic acid encoding a juxtamembrane is repeated one or more times in the same orientation. The above repeat nucleotide sequences can be lined up one directly after another, or they can contain optional nucleotide sequences between each of the repeat nucleotide sequences. In addition, the number of duplicated base is not particularly limited. Furthermore, although mutations of deletion, substitution or addition of one or more bases can exist in a portion of a nucleotide sequence between the corresponding tandem duplications. In the tandem duplication of the present invention, the tandem duplication may be detected as length mutation. For example, the tandem duplication is contained in cDNA having nucleotide sequences of SEQ ID NOs: 6 to 10, and in genomic DNA having nucleotide sequences of SEQ ID NOs: 11 to 15 as nucleic acids encoding a juxtamembrane.

Figure 2:
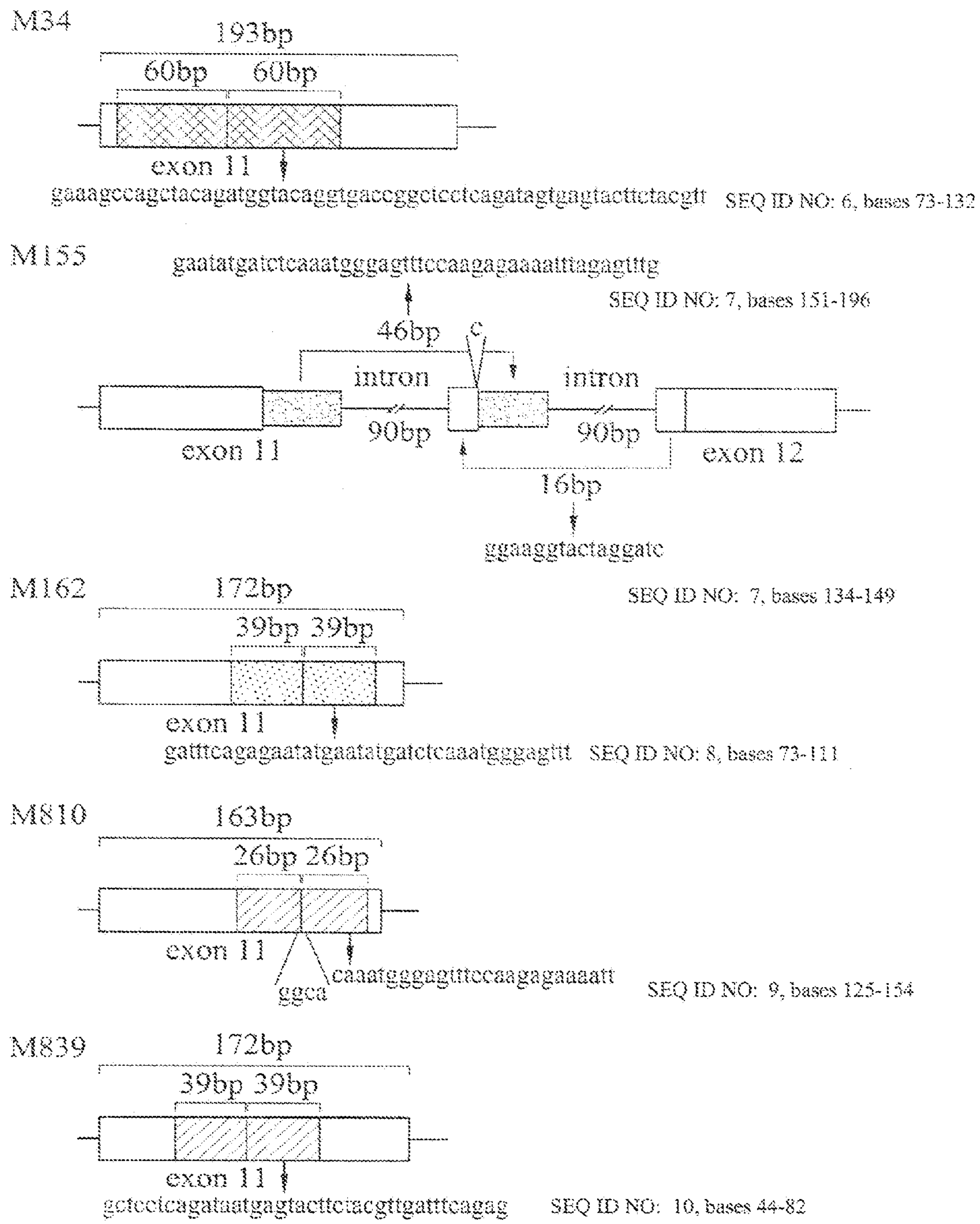
FIG. 2 is a schematic view showing tandem duplication at exon 11 and exon 12 for M34, M155, M162, M810 and M839.

Nucleic acids (cDNA or genomic DNA) having tandem duplication which are newly found in a nucleotide sequence of the juxtamembrane of FLT3 are named M34 (SEQ ID NOs: 6 and 11), M155 (SEQ ID NOs: 7 and 12), M162 (SEQ ID NOs: 8 and 13), M810 (SEQ ID NOs: 9 and 14) and M839 (SEQ ID NOs: 10 and 15), respectively, and their schematic view is shown in FIG. 2. Incidentally, it is desired that the tandem duplication in the present invention takes place in-frame. Amino acid sequences encoded by the above SEQ ID NOs: 6 to 10 are shown in SEQ ID NOs: 1 to 5.

The nucleic acid of the present invention concerns a nucleic acid encoding a receptor protein kinase, wherein the nucleic acid has the tandem duplication as described above in a nucleotide sequence of a juxtamembrane, particularly a nucleic acid of FMS-like tyrosine kinase 3 (FLT3) mutant, wherein the nucleic acid has the tandem duplication in a nucleotide sequence of a juxtamembrane. The amino acid sequences of a juxtamembrane having the tandem duplication are shown by e.g. SEQ ID NOs: 1 to 5 as mentioned above, and the nucleic acids of the present invention are those comprising nucleotide sequences encoding these amino acid sequences. Concretely, for example, the present nucleic acids are those comprising nucleotide sequences shown by SEQ ID NOs: 6 to 15. More particularly, a nucleic acid of a tandem duplication mutant of FLT3 comprising a nucleic acid of a juxtamembrane includes, for example, nucleic acids encoding tandem duplication mutants of FLT3 shown by SEQ ID NOs: 16 to 20, more concretely, nucleic acids comprising nucleotide sequences encoding tandem duplication mutants of FLT3 shown by SEQ ID NOs: 21 to 25. In addition, they may be a nucleic acid capable of hybridizing to the above nucleic acid under stringent conditions, and having tandem duplication in a nucleotide sequence encoding a juxtamembrane.

Furthermore, the nucleic acid of the present invention concerns a nucleic acid encoding a juxtamembrane and having tandem duplication, the nucleic acid including, for example, a nucleic acid having tandem duplication, wherein the nucleic acid encodes amino acid sequences shown by SEQ ID NOs: 1 to 5, concretely, nucleic acids shown by SEQ ID NOs: 6 to 15, or a nucleic acid has tandem duplication capable of hybridizing to those nucleic acids under stringent conditions.

Here, hybridizing under stringent conditions refers to hybridization with the nucleic acids, wherein the hybridization comprises, for example, incubating a nucleic acid-immobilized membrane with a probe at 50° C. for 12 to 20 hours in 6×SSC, wherein 1×SSC indicates 0.15 M NaCl, 0.015 M sodium citrate, pH 7.0, containing 0.5% SDS, 0.1% bovine serum albumin (BSA), 0.1% polyvinyl pyrrolidone, 0.1% Ficol 400, and 0.01% denatured salmon sperm DNA, but not limited to the above conditions.

The nucleic acid of the present invention can be obtained by, e.g. the following method.

First, cells in which length mutation takes place are detected by synthesizing cDNA by a reverse transcriptase with RNA as a template, the RNA purified from various pathologic cells, particularly leukemia cells, thereafter carrying out DNA amplification reaction using primers which are targeted to a region encoding a juxtamembrane of a desired receptor protein kinase, and comparing the length of the amplified DNA fragments by means of an electrophoresis method. Further, it is possible to identify whether or not a mutation is tandem duplication by determining a nucleotide sequence of the obtained amplified DNA fragment.

Next, cDNA encoding a receptor protein kinase, the cDNA having novel tandem duplication of the present invention can be obtained by synthesizing cDNA by a reverse transcriptase with RNA obtained from cells in which tandem duplication takes place, thereafter carrying out DNA amplification reaction using primers which can specifically amplify cDNA of a desired receptor protein kinase.

The nucleic acid of the present invention can be also obtained by using genomic DNA as a template, the genomic DNA purified from pathologic cells.

In the present invention, leukemia cells are selected as the pathologic cells, and FLT3 is preferably targeted as the receptor protein kinase.

An FLT3 gene comprises 21 exons, and alternatively, the juxtamembrane is encoded in 18 bp at 3'-side of exon 10 and 117 bp at 5'-side of exon 11 [O. Rosnet, et al., Oncogene, 6, 1641-1650 (1991)]. Primers covering the region of exon 11 and exon 12 can be selected as primers used in DNA amplification reaction, Examples of the nucleotide sequences are shown in SEQ ID NOs: 26 and 27. Incidentally, exon 12 and 16 bp at 3'-side of exon 11 encode a partial portion of the tyrosine kinase domain.

DNA amplified fragments as shown by SEQ ID NOs: 6 to 10 are obtained when RNA is used as a template for DNA amplification reaction, and DNA amplified fragments as shown by SEQ ID NOs: 11 to 15 are obtained when genomic DNA is used as a template. As a result, it is confirmed that these resulting fragments have in-frame tandem duplication within exon 11 or exons 11 to 12.

Alternatively, nucleotide sequences of cDNA encoding a whole length of FLT3 and having the above in-frame tandem duplication are shown in SEQ ID NOs: 21 to 25.

The polypeptide of the present invention is a polypeptide encoded by the above nucleic acids. Concretely, there can be exemplified a polypeptide comprising amino acid sequences of SEQ ID NOs: 1 to 5, and tandem duplication mutants of FLT3 as shown by SEQ ID NOs: 16 to 20.

The polypeptide of the present invention can be obtained by purifying from cells expressing the polypeptide, and can be also obtained by employing a conventional gene engineering procedures. A tandem duplication mutant of FLT3, for example, can be obtained by inserting the above nucleic acids into a suitable expression vector, and then expressing the product in a suitable host. In addition, a polypeptide with only a juxtamembrane of a receptor protein kinase of the present invention can be obtained by inserting a DNA fragment encoding a juxtamembrane alone to the above expression vector.

Further, the polypeptide of the present invention can be expressed as a fusion protein. For instance, in order to increase amounts of expression of a desired protein, N-terminal peptide chain derived from other protein is added to N-terminus of the desired protein, or a suitable peptide chain is added to N-terminus or C-terminus of the desired protein to express the resulting polypeptide, so that purification of the desired protein using a resin carrier having affinity to the peptide chain can be facilitated.

The present polypeptide also encompasses a polypeptide encoded by a nucleic acid having tandem duplication in a nucleotide sequence of a juxtamembrane, wherein the polypeptide results from at least one of deletion, substitution or addition of one or more amino acid residues in amino acid sequences of the present invention, e.g. SEQ ID NOs: 1 to 5, 1.6 to 20 in Sequence Listing. In other words, there can be a case where no mutations take place in amino acid sequences in the region encoded by tandemly duplicated nucleic acids, and deletion, substitution or addition of amino acid residues takes place in other portions of amino acid sequences; or a case where deletion, substitution or addition of amino acid residues takes place in amino acid sequences of the region encoded by tandemly duplicated nucleic acids. Introduction of deletion, substitution or addition of the amino acid residues can be easily carried out by introducing mutation into the desired nucleic acid sequence by a method using restriction endonucleases, nucleases and the like, or a method for performing site-directed mutagenesis [W. Ito, et al., *Gene,* 102, 67-70 (1991)] etc., thereby incorporating the mutated nucleic acid sequence into an expression vector to express the product in a suitable host cell.

In the present invention, the antibody refers to an antibody capable of specifically binding to a region encoded by a nucleic acid having tandem duplication occurring in a nucleotide sequence of a juxtamembrane of the receptor protein kinase. In order to obtain the antibody, for example, the antibody is obtained as anti-serum by immunizing animals with a peptide having amino acid sequences of SEQ ID NOs: 1 to 5 together with adjuvant by conventional method. In addition, the antibody can be obtained as a monoclonal antibody by a method described in G. Galfare, et al., *Nature,* 266, 550-552 (1997).

In the present invention, the nucleic acid capable of specifically binding to nucleic acids having tandem duplication occurring in a nucleotide sequence of a juxtamembrane of the receptor protein kinase is not to be particularly limited, and is exemplified by anti sense DNA of double stranded DNA having tandem duplication or RNA corresponding to the antisense DNA.

The method for detection of a nucleic acid of the present invention comprises the following steps:

step (a): obtaining a human nucleic acid sample;

step (b): subjecting the nucleic acid sample obtained in the above step (a) to gene amplification reaction to provide a nucleic acid fragment obtained by amplifying a region having tandem duplication in a juxtamembrane, wherein the region can be found in a nucleic acid encoding a receptor protein kinase; and step (c): examining the presence of tandem duplication for the nucleic acid fragment of the above step (b).

First, step (a) will be described. The human nucleic acid sample usable in the present invention is not to be particularly limited, as long as it is a nucleic acid encoding a receptor protein kinase, the nucleic acid having tandem duplication in a nucleotide sequence of a juxtamembrane, such as genomic DNA, cDNA or mRNA. The human nucleic acid sample can be prepared by conventionally performed known method, including, for instance, a method described in *Molecular cloning: A LABORATORY MANUAL,* 2nd eds. (T. Maniatis et al., Cold Spring Harbor Laboratory Press, published in 1989).

Secondly, step (b) will be described. The nucleic acid sample and suitable primers are used to amplify a nucleic acid encoding a region containing mutation site which can be found in a juxtamembrane of the receptor protein kinase of the interest to obtain a desired nucleic acid fragment. A method for performing DNA amplification reaction usable in this step is not particularly limited, as long as it is a method capable of amplifying the above region, and there can be utilized nucleic acid amplification methods, such as a nucleic acid amplification method utilizing RT-PCR method, PCR method, or RNA polymerases (Japanese Patent Laid-Open Nos. Hei 2-5864 and Hei 7-203999), or strand substitution amplification method (Japanese Examined Patent Publication No. Hei 7-114718, and Japanese Patent Laid-Open No. Hei 7-88242). Among them, the RT-PCR method or PCR method is preferably used.

The region to be amplified having tandem duplication in a juxtamembrane includes, for example, in case of FLT3, a region containing a whole or partial portion of the region from 18 bp at 3'-side of exon 10 to 117 bp at 5'-side of exon 11, without being particularly limited thereto as long as the region contains an exon 11 site.

The primers used in RT-PCR method or PCR method are not particularly limited as long as they are primers capable of amplifying a DNA fragment containing the above mutation site. Concretely, there can be exemplified a primer pair having nucleotide sequences as shown in SEQ ID NOs: 26 and 27 in Sequence Listing. In addition, PCR conditions are not particularly limited, and conventionally performed known conditions can be used on PCR reaction.

Thirdly, step (c) will be described. In this step, the presence of tandem duplication for the nucleic acid fragment obtained in step (b) is examined. The method for detection of the presence of tandem duplication is not particularly limited, and it is preferable that a method of comparing lengths of amplified DNA fragments by means of agarose gel electrophoresis method is used.

In addition, a method for examining single strand conformation polymorphism (SSCP) can be used as a method for detection of mutation which is usable in this step. The method comprises examining the differences of a higher-order structure as the differences of mobility in electrophoresis, wherein the high-order structure is dependent on a nucleotide sequence in which single-stranded DNA is formed by intramolecular interaction (*Proc. Natl. Acad. Sci. USA,* 86: 2766-2770, 1989). The presence or absence of mutation can be detected by subjecting the nucleic acid fragment obtained in step (b) to electrophoresis under conditions described in the above-mentioned publication, and comparing its mobility with that of a nucleic acid fragment derived from a normal receptor protein kinase.

Other detection methods include a method in which the above step (c) is altered to other method for detection of mutation. For the detection of mutation, there can be used a known method for detection of mutation, such as hybridization method using a suitable DNA fragment containing a mutation site as a probe, or DGGE method [val C. Sheffield et al., *Proc. Natl. Acad. Sci. USA* 86, 232-236 (1989)]. In addition, a method for detection of mutation using a MutS protein is known (Japanese Patent Laid-Open No. Hei 7-327698).

The mutation can be identified by sequencing the nucleotide sequence for DNA fragment in which a length mutation is confirmed by means of the above-mentioned method. For sequencing the nucleo-tide sequence, a conventionally used method can be employed, including, for example, a method comprising cloning an amplified DNA fragment into a suitable vector and determining the nucleotide sequence, or a method for determining the nucleotide sequence using an amplified fragment per se as a template.

As described above, the present invention provides a use of a nucleic acid of the present invention described above for detection of a nucleic acid encoding a receptor protein kinase, wherein the nucleic acid has tandem duplication in a nucleotide sequence of a juxtamembrane.

The method for detection of a nucleic acid of the present invention can be utilized in diagnosis of M2, M4, and M5 based on the FAB (French-American-British) classification of acute myeloid leukemia (AML). Based on the FAB (French-American-British) classification, pathologic types of AML are classified into six classes as M1 (myeloblastic, no maturation potential), M2 (myeloblastic, with maturation potential), M3 (promyelocytic), M4 (myelomonocytic), M5 (monocytic), and M6 (erythroleukemia) (Shin Rinsho Kensa Gishi Koza, 10, Ketsuekigaku, 75, Igaku-Shoin).

It is understood that patients harboring an FLT3 gene having the tandem duplication of the present invention belong to classes M2, M4, and M5 above, and that the patients relapse into symptom to death even with transient symptom remission, so that their prognosis leads to mal-consequence. Therefore, according to the detection method of the present invention, there can be provided a method for examination useful to the pathologic judgment of AML.

Incidentally, of the above patients, the detection of mutation using genomic DNA from myelocyte of a patient obtained at the time of symptom remission is carried out, and as a result, tandem duplications in a juxtamembrane are not found. This mutation is therefore assumed to be a somatic mutation.

Also, the nucleic acid of the present invention, which has tandem duplication, serves as a marker for myelodysplastic syndrome (MDS), which develops in the pre-stage of leukemia, AML with dysplasia, and the like, as well as AML as classified based on the FAB classification. The detection method of the present invention therefore is a method for examination which is useful for the pathologic judgment of these diseases.

By utilizing the above detection method, there can be provided a kit for detection of a nucleic acid of the present invention. Concretely, there is a kit for detection of a nucleic acid by the above described detection method, the nucleic acid encoding a receptor protein kinase and having tandem duplication in the nucleotide sequence of a juxtamembrane, characterized in that the kit comprises primers for amplifying a region having tandem duplication, wherein the region can be found on the receptor protein kinase gene.

The diagnosis of the above AML etc. can be easily carried out by using such a kit.

In the present invention, a polypeptide encoded by a nucleic acid having tandem duplication as described above can be further detected by the steps shown below:

step 1: obtaining a human protein sample; and step 2: examining the presence of tandem duplication in the nucleotide sequence of a juxtamembrane of the protein sample obtained in the above step 1.

First, step 1 will be described. The human protein sample can be prepared by preparing a membrane protein from a cell which is assumed to have the polypeptide of the present invention expressed therein (e.g., leukemic cell, in case of FLT3).

Second, step 2 will be described. The method for detection of tandem duplication mutations is not particularly limited, and can be carried out by using a labeled antibody capable of specifically binding to the juxtamembrane encoded by a nucleic acid having a tandem duplication mutation.

This step can, for example, be carried out by a method comprising subjecting the protein sample obtained in step 1 to SDS-PAGE to separate proteins, and subsequently detecting the desired protein by immunoblotting method.

In another embodiment of the present invention, there can be provided a method for regulating the proliferation, immune response and signal information transmission of leukemic cells, hematopoietic stem cells, etc. using the above nucleic acids or polypeptides, or nucleic acids or antibodies capable of specifically binding thereto.

Among them, a preferred embodiment includes an application to immunotherapy for tumors Conventionally, it has been known that tumor-specific peptides of proteins specifically expressed in tumor cells serve as targets of T cell immune responses to tumor cells. In a method for performing the application, the techniques described in the following reports, for example, can be utilized. Concretely, CD4+T cells restricted to HLA-DR are isolated, the cells specifically reacting with ras peptide resulting from substitution of 12th amino acid glycine with another amino acid in the human T cells (Jung, S., *J. Exp. Med.* 173, 273, 1991), and a CTL (cytotoxic T lymphocyte) recognizing a peptide consisting of eight amino acids including the mutation site for 61th amino acid mutation can be derived from a mouse immunized with a recombinant vaccinia virus capable of producing ras protein, which has mutation at 61th amino acid (Skipper, J., *J. Exp. Med.* 177, 1493, 1993). In addition, in a mouse immunized with a soluble mutant ras protein prepared by gene recombination, the in vivo proliferation of tumor cells having the same mutation is suppressed (Fenton, R. G., *J. Natl. Cancer Inst.* 85, 1294, 1993), and a CTL showing cytotoxic activity against tumor cells expressing the same mutant ras can be obtained from splenocytes sensitized with the mutant ras peptide (Peace, D. J., *J. Exp. Med.* 179, 473, 1994). On the other hand, the bcr-abl chimeric protein, which is often detected in chronic myelocytic leukemia, possesses high tyrosine kinase activity and plays a key role in the onset of leukemia and the proliferation of leukemic cells. By immunizing with a peptide in the vicinity of the fusion site of this fusion protein, T cells reactive to this fusion protein can be obtained (Chen, W., *Proc. Natl. Acad. Sci. USA* 89, 1468, 1992). Moreover, antisense DNA or RNA corresponding to the fusion gene is capable of suppressing the proliferation of tumors expressing this gene in vivo (Skorski, T., *Proc. Natl. Acad. Sci. USA* 91, 4504, 1994).

It is therefore possible to obtain T cells reactive to a receptor protein kinase comprising the peptide of the present invention, wherein the peptide is encoded by a nucleic acid having tandem duplication occurring in the nucleotide sequence of a juxtamembrane, and to regulate the proliferation of cells that express the above kinase by immunizing with the above peptide.

Also, when the presence of the tandem duplication of the present invention is involved in cell proliferation regulation, it is possible to regulate the signaling mechanism with antisense DNA or RNA for the above gene to regulate cell proliferation.

When binding a ligand to an extracellular region, the receptor protein kinase undergoes a conformational change to form a dimer, resulting in increased kinase domain activity in the intracellular region, whereby self-phosphorylation or phosphorylation of a substrate of the above kinase takes place. In these steps, various signaling molecules are involved, and the information transmitted into cells causes various biological phenomena, such as cell morphological change, cell movement, morphogenesis, cell proliferation, malignant alteration, differentiation, and apoptosis. Acute myelocytic leukemic cells of high malignancy have been reported to possess strong affinity to the FLT3 ligand and promote cell proliferation (Piacibello, W., *Blood* 86, 4105, 1995; Lisovsky, M., *Blood* 86, 22a, 1995; McKenna, H., *J. Exp. Hematol.* 24, 378, 1996; Dehmel, U., *Leukemia* 10, 261, 1996). In cells expressing the FLT3 tandem duplication mutant of the present invention, it is expected that the system for signaling from the FLT3 ligand is highly activated. Hematopoietic stem cells that express the mutant are therefore provided as a source of hematopoietic stem cells possessing strong proliferation potential. By comparing the hematopoietic stem cells with cells expressing the normal FLT3, materials and methods suitable for screening for various drugs can be provided.

As described above, by utilizing a method of the present invention, it is applicable to the examination and treatment of blood cell diseases, hematopoietic stem cell diseases, and other diseases.

The present invention will be hereinafter described in more detail by means of examples, but the present invention is not limited by those examples.

EXAMPLE 1

1) Analysis of FLT3 Gene Expression Pattern

On 80 cases of acute leukemia patients (50 cases of child ALL, 30 cases of adult AML), analysis of FLT3 gene expression was carried out by RT-PCR method. The primers used were designed to have nucleotide sequences as shown by SEQ ID NOs: 26 and 27 in Sequence Listing, and to completely cover and amplify a transmembrane region through a juxtamembrane. By using the above primer pair, the resulting amplified DNA product is 366 bp in length, when normal FLT3 has been transcribed.

Figure 1:
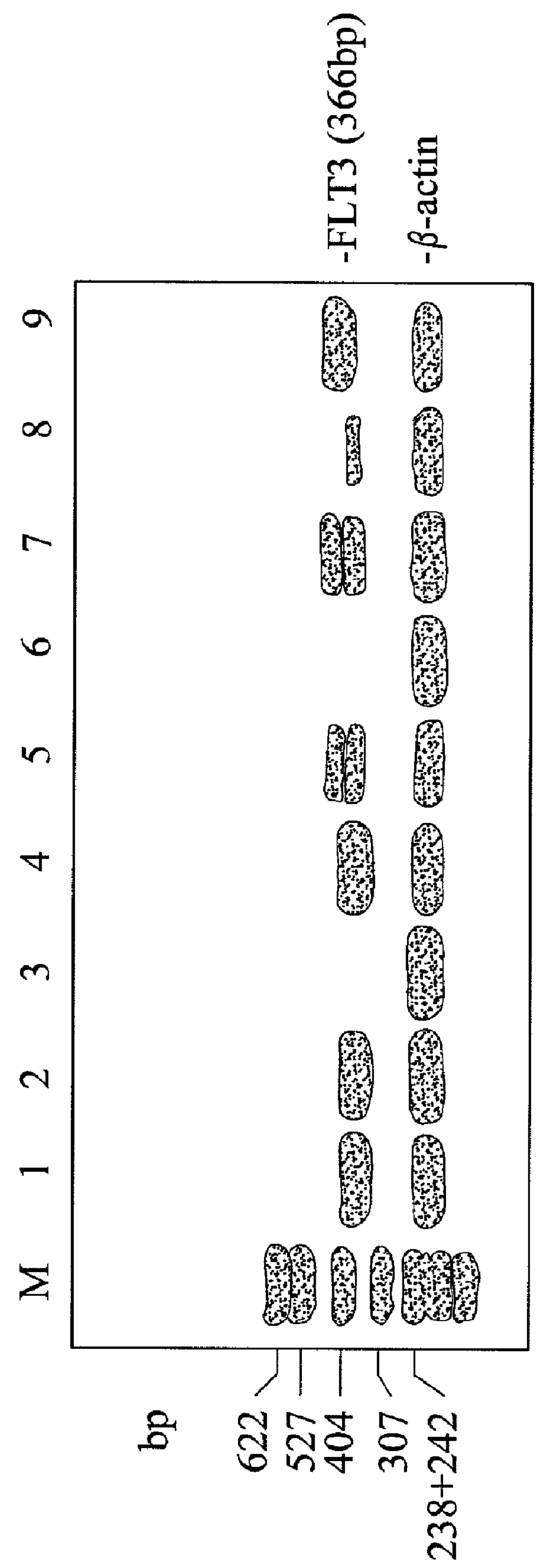
FIG. 1 is a view showing agarose gel electrophoresis of the case where RT-PCR is carried out with RNA obtained from leukemic cells derived from AML patients as a template. In the figure, lanes 1 to 5 respectively show results for patients belonging to M1, M2, M3, M4 and M5 (M34 patients) on FAB classification, and lanes 6 to 9 respectively show results for M1, M2 (M155 patients), M3 and M4 (M162 patients).

A total RNA was extracted from a peripheral blood or myelocyte derived from the above patient with a Trizol reagent (manufactured by LifeTech), followed by DNA amplification reaction using an RT-PCR kit (manufactured by Takara Shuzo Co., Ltd.) and Thermal Cycler (manufactured by Takara Shuzo Co., Ltd.) under following conditions. cDNA was synthesized from a total RNA using a reverse transcriptase. In 50 μl of a reaction mixture containing 1 μl of the cDNA (equivalent to 40 ng of a total RNA), 200 μM dNTP mixture, 1× PCR buffer, 2 U of Taq DNA polymerase, and 20 pmol each of the above-described primers, the above reaction mixture was heated at 94° C. for 5 minutes, and thereafter repeated 35 times of a thermal cycle consisting of 64° C. for 30 seconds, 72° C. for 45 seconds, and 94° C. for 30 seconds, and then finally treated at 72° C. for 5 minutes. To check quality of RNA, RT-PCR was carried out in the same manner except that a pair of the primers shown by SEQ ID NOs: 28 and 29 in Sequence Listing were used, with β-actin as the target. The amplified DNA products thus obtained were subjected to electrophoresis on 2 to 3 agarose gel (manufactured by FMC) containing ethidium bromide, and detected under UV irradiation. One example of electrophoresis pattern is shown in FIG. 1, and the results are shown in Table 1.

TABLE 1

| FAB subtype | Number of cases examined | Number of positive mRNA expression of of FLT3 (%) | Length mutation (%) |
|---|---|---|---|
| AML tota1 | 30 | 22 (73%) | 5 (17%) |
| M1 | 3 | 2 (67%) | 0 |
| M2 | 9 | 7 (78%) | 1 (14%) |
| M3 | 8 | 5 (63%) | 0 |
| M4 | 5 | 4 (80%) | 2 (40%) |
| M5 | 4 | 3 (75%) | 2 (50%) |
| N6 | 1 | 1 (100%) | 0 |
| ALL total | 50 | 39 (78%) | 0 |
| cALL | 27 | 24 (89%) | 0 |
| pre-B ALL | 13 | 11 (85%) | 0 |
| B-ALL | 1 | 0 | 0 |
| T-ALL | 9 | 4 (44%) | 0 |

It is found from table 1 that the transcription product of the FLT3 gene was found in 39 cases (78%) of the 50 ALL cases and 22 cases (73%) of the 30 AML cases. Among them, the amplified DNA product longer than the expected 366 bp was detected in 5 cases (23%) of the 22 FLT3-positive AML cases, so that a length mutation in FLT3 gene was observed. Incidentally, in four cases (M34, M155, M810, and M839), the expected 366 bp band and a longer band than the expected were detected. In one case (M162), the 366 bp band was not detected, and a longer band alone was detected.

2) Analysis of Nucleotide Sequence of Length Mutation Product of FLT3 Gene

To examine in more detail length mutations in the gene in the above 5 cases, the amplified DNA product was purified from agarose gel, and nucleotide sequences of the exon 11 and exon 12 regions were determined. As a result, it was confirmed that these length mutations resulted from tandem duplications in nucleotide sequences of the respective juxtamembrane. Concretely, a 39 bp or 60 bp tandem duplication within exon 11 was found in cases M34, M162, and M839; and a 26 bp tandem duplication including a 4 bp (GGCA) insert was found in case M810. In addition, case M155 was found to have a 63 bp tandem duplication comprising the first 16 bp of exon 12 immediately after exon 11, one cytosine residue insert, and the last 46 bp of exon 11. The nucleotide sequences obtained are shown in SEQ ID NOs: 6 to 10 in Sequence Listing, and a schematic view of these tandem duplications is shown in FIG. 2.

Characteristically, these tandem duplications occur in-frame, and these mutations are reflected in the actually expressed polypeptides. The amino acid sequences encoded by these nucleotide sequences are shown in SEQ ID NOs: 1 to 5.

3) Analysis of Nucleotide Sequence of Genomic DNA

Amplified DNA products obtained by PCR with FLT3 genomic DNA derived from myelocytes from the above 5 cases of patients as templates were analyzed. PCR reaction was carried out under amplification conditions such that 2 U of Taq DNA polymerase (Takara Shuzo Co., Ltd.) was added to a PCR buffer containing 50 ng of genomic DNA, 200 μM of a dNTP mixture, and 20 pmol of each of primers, to make up a total volume of 50 μl. For exons 10 to exon 19, each exon was individually subjected to amplification DNA reaction. The length mutation was observed in same manner as that when mRNA was analyzed in the case where exon 11 and exon 12 were amplified with primers of SEQ ID NOs: 30 and 31, and primers of SEQ ID NOs: 32 and 33 in Sequence Listing as pairs. When the PCR products were purified using QIAEXII (QIAGEN), cloned into pCRII vector (Invitrogen), and subjected to nucleotide sequence analysis, similar results to those with the nucleotide sequences of cDNA (SEQ ID NOs: 21 to 25) were obtained. The results are collectively shown in FIG. 2.

EXAMPLE 2

Analysis of Mutations in Juxtamembrane of Receptor Protein Kinase and their Pathologic Relationship To analyze mutations in a juxtamembrane of the receptor protein kinase and their pathologic relationship, the relationship between the pathologic classification of symptoms and FLT3 gene is shown in Table 1. Five cases showing tandem duplication in the nucleotide sequence of a juxtamembrane belonged to M2 (myeloblastic, with maturation potential), M4 (myelomonocytic), or M5 (monocytic) based on the FAB classification, and all of them were cases in which patients relapse into symptom to death even with transient symptom remission.

The nucleotide sequences of exon regions encoding tyrosine kinase domain were also analyzed, and no mutations were found in these regions.

Therefore, it was suggested that the in-frame tandem duplications in gene region encoding a juxtamembrane of FLT3 were associated with AML with monocyte growth was suggested.

Also, since such length mutations were not detected in DNA samples from myelocytes collected from three cases (M34, M162, and M810) at the time of complete remission, the tandem duplication of the present invention was found to be a somatic mutation.

Industrial Applicability

According to the present invention, there can be provided a novel receptor protein kinase having tandem duplication mutation in the nucleotide sequence of a juxtamembrane, and its nucleotide sequence and amino acid sequence information. In addition, there can be provided pathological diagnoses, a method for examination of leukemia etc. utilizing the present invention, a kit and a reagent for examination related thereto. Furthermore, there can be provided a method for regulating and analyzing conditions of proliferation and differentiation, malignant alteration, immune response, and signalling for cells represented by hematopoietic stem cells and leukemia cells utilizing the present invention, and a kit and a reagent related thereto.

What is claimed:

1. A method of diagnosing acute myeloid leukemia (AML) in a human subject, which comprises:

obtaining from the human subject a sample which comprises nucleic acid, wherein the nucleic acid comprises genomic DNA, cDNA or RNA;

detecting from the sample an isolated nucleic acid which encodes human FLT3 kinase, or detecting from the sample an isolated nucleic acid fragment of a nucleic acid which encodes human FLT3 kinase, wherein said isolated nucleic acid or said isolated nucleic acid fragment comprises at least one in frame tandem duplication located within the nucleic acid region encoding a juxtamembrane domain of human FLT3 kinase, said nucleic acid region is amplified by primers SEQ ID NO: 26 and SEQ ID NO: 27, wherein said isolated nucleic acid and said isolated nucleic acid fragment are markers for AML; and diagnosing AML in the human subject based on the presence of the in frame tandem duplication in the isolated nucleic acid or nucleic acid fragment.

2. The method of diagnosing AML in the human subject according to claim 1, wherein the in frame tandem duplication is detected is detected by sequencing.

3. The method of diagnosing AML in the human subject according to claim 1, wherein said in frame tandem duplication is detected is detected by gel electrophoresis.

* * * * *

```
                          SEQUENCE LISTING


<160> NUMBER OF SEQ ID NOS: 33

<210> SEQ ID NO 1
<211> LENGTH: 97
<212> TYPE: PRT
<213> ORGANISM: Homo sapiens

<400> SEQUENCE: 1

Gln Phe Arg Tyr Glu Ser Gln Leu Gln Met Val Gln Val Thr Gly Ser
  1               5                  10                  15

Ser Asp Asn Glu Tyr Phe Tyr Val Glu Ser Gln Leu Gln Met Val Gln
             20                  25                  30

Val Thr Gly Ser Ser Asp Ser Glu Tyr Phe Tyr Val Asp Phe Arg Glu
         35                  40                  45

Tyr Glu Tyr Asp Leu Lys Trp Glu Phe Pro Arg Glu Asn Leu Glu Phe
     50                  55                  60

Gly Lys Val Leu Gly Ser Gly Ala Phe Gly Lys Val Met Asn Ala Thr
65                  70                  75                  80

Ala Leu Glu Leu Ala Lys Gln Glu Ser Gln Ser Arg Leu Pro Ser Lys
                 85                  90                  95

Cys


<210> SEQ ID NO 2
<211> LENGTH: 100
<212> TYPE: PRT
<213> ORGANISM: Homo sapiens

<400> SEQUENCE: 2

Gln Phe Arg Tyr Glu Ser Gln Leu Gln Met Val Gln Val Thr Gly Ser
  1               5                  10                  15

Ser Asp Asn Glu Tyr Phe Tyr Val Asp Phe Arg Glu Tyr Glu Tyr Asp
             20                  25                  30

Leu Lys Trp Glu Phe Pro Arg Glu Asn Leu Glu Phe Gly Lys Val Leu
         35                  40                  45

Gly Ser Glu Tyr Asp Leu Lys Trp Glu Phe Pro Arg Glu Asn Leu Glu
     50                  55                  60

Phe Gly Lys Val Leu Gly Ser Gly Ala Phe Gly Lys Val Met Asn Ala
65                  70                  75                  80

Thr Ala Tyr Gly Ile Ser Lys Thr Gly Val Ser Ile Gln Val Ala Val
                 85                  90                  95

Lys Met Leu Lys
            100


<210> SEQ ID NO 3
<211> LENGTH: 92
<212> TYPE: PRT
<213> ORGANISM: Homo sapiens
```

```
<400> SEQUENCE: 3

Gln Phe Arg Tyr Glu Ser Gln Leu Gln Met Val Gln Val Thr Gly Ser
  1               5                  10                  15

Ser Asp Asn Glu Tyr Phe Tyr Val Asp Phe Arg Glu Tyr Glu Tyr Asp
             20                  25                  30

Leu Lys Trp Glu Phe Asp Phe Arg Glu Tyr Glu Tyr Asp Leu Lys Trp
         35                  40                  45

Glu Phe Pro Arg Glu Asn Leu Glu Phe Gly Lys Val Leu Gly Ser Gly
     50                  55                  60

Ala Phe Gly Lys Val Met Asn Ala Thr Ala Tyr Gly Ile Ser Lys Thr
65                  70                  75                  80

Gly Val Ser Ile Gln Val Ala Val Lys Met Leu Lys
                 85                  90


<210> SEQ ID NO 4
<211> LENGTH: 89
<212> TYPE: PRT
<213> ORGANISM: Homo sapiens

<400> SEQUENCE: 4

Gln Phe Arg Tyr Glu Ser Gln Leu Gln Met Val Gln Val Thr Gly Ser
  1               5                  10                  15

Ser Asp Asn Glu Tyr Phe Tyr Val Asp Phe Arg Glu Tyr Glu Tyr Asp
             20                  25                  30

Leu Lys Trp Glu Phe Pro Arg Glu Asn Trp His Lys Trp Glu Phe Pro
         35                  40                  45

Arg Glu Asn Leu Glu Phe Gly Lys Val Leu Gly Ser Gly Ala Phe Gly
     50                  55                  60

Lys Val Met Asn Ala Thr Ala Tyr Gly Ile Ser Lys Thr Gly Val Ser
65                  70                  75                  80

Ile Gln Val Ala Val Lys Met Leu Lys
                 85


<210> SEQ ID NO 5
<211> LENGTH: 92
<212> TYPE: PRT
<213> ORGANISM: Homo sapiens

<400> SEQUENCE: 5

Gln Phe Arg Tyr Glu Ser Gln Leu Gln Met Val Gln Val Thr Gly Ser
  1               5                  10                  15

Ser Asp Asn Glu Tyr Phe Tyr Val Asp Phe Arg Gly Ser Ser Asp Asn
             20                  25                  30

Glu Tyr Phe Tyr Val Asp Phe Arg Glu Tyr Glu Tyr Asp Leu Lys Trp
         35                  40                  45

Glu Phe Pro Arg Glu Asn Leu Glu Phe Gly Lys Val Leu Gly Ser Gly
     50                  55                  60

Ala Phe Gly Lys Val Met Asn Ala Thr Ala Tyr Gly Ile Ser Lys Thr
65                  70                  75                  80

Gly Val Ser Ile Gln Val Ala Val Lys Met Leu Lys
                 85                  90


<210> SEQ ID NO 6
<211> LENGTH: 296
<212> TYPE: DNA
<213> ORGANISM: Homo sapiens
```

<400> SEQUENCE: 6
caatttaggt atgaaagcca gctacagatg gtacaggtga ccggctcctc agataatgag 60
tacttctacg ttgaaagcca gctacagatg gtacaggtga ccggctcctc agatagtgag 120
tacttctacg ttgatttcag agaatatgaa tatgatctca aatgggagtt tccaagagaa 180
aatttagagt ttgggaaggt actaggatca ggtgcttttg gaaaagtgat gaacgcaaca 240
gctttggaat tagcaaaaca ggagtctcaa tccaggttgc cgtcaaaatg ctgaaa 296

<210> SEQ ID NO 7
<211> LENGTH: 300
<212> TYPE: DNA
<213> ORGANISM: Homo sapiens

<400> SEQUENCE: 7
caatttaggt atgaaagcca gctacagatg gtacaggtga ccggctcctc agataatgag 60
tacttctacg ttgatttcag agaatatgaa tatgatctca aatgggagtt tccaagagaa 120
aatttagagt ttgggaaggt actaggatcc gaatatgatc tcaaatggga gtttccaaga 180
gaaaatttag agtttgggaa ggtactagga tcaggtgctt ttggaaaagt gatgaacgca 240
acagcttatg gaattagcaa aacaggagtc tcaatccagg ttgccgtcaa aatgctgaaa 300

<210> SEQ ID NO 8
<211> LENGTH: 276
<212> TYPE: DNA
<213> ORGANISM: Homo sapiens

<400> SEQUENCE: 8
caatttaggt atgaaagcca gctacagatg gtacaggtga ccggctcctc agataatgag 60
tacttctacg ttgatttcag agaatatgaa tatgatctca aatgggagtt tgatttcaga 120
gaatatgaat atgatctcaa atgggagttt ccaagagaaa atttagagtt tgggaaggta 180
ctaggatcag gtgcttttgg aaaagtgatg aacgcaacag cttatggaat tagcaaaaca 240
ggagtctcaa tccaggttgc cgtcaaaatg ctgaaa 276

<210> SEQ ID NO 9
<211> LENGTH: 267
<212> TYPE: DNA
<213> ORGANISM: Homo sapiens

<400> SEQUENCE: 9
caatttaggt atgaaagcca gctacagatg gtacaggtga ccggctcctc agataatgag 60
tacttctacg ttgatttcag agaatatgaa tatgatctca aatgggagtt tccaagagaa 120
aattggcaca aatgggagtt tccaagagaa aatttagagt ttgggaaggt actaggatca 180
ggtgcttttg gaaaagtgat gaacgcaaca gcttatggaa ttagcaaaac aggagtctca 240
atccaggttg ccgtcaaaat gctgaaa 267

<210> SEQ ID NO 10
<211> LENGTH: 276
<212> TYPE: DNA
<213> ORGANISM: Homo sapiens

<400> SEQUENCE: 10
caatttaggt atgaaagcca gctacagatg gtacaggtga ccggctcctc agataatgag 60
tacttctacg ttgatttcag aggctcctca gataatgagt acttctacgt tgatttcaga 120
gaatatgaat atgatctcaa atgggagttt ccaagagaaa atttagagtt tgggaaggta 180

```
ctaggatcag gtgcttttgg aaaagtgatg aacgcaacag cttatggaat tagcaaaaca    240

ggagtctcaa tccaggttgc cgtcaaaatg ctgaaa                              276
```

```
<210> SEQ ID NO 11
<211> LENGTH: 386
<212> TYPE: DNA
<213> ORGANISM: Homo sapiens

<400> SEQUENCE: 11

caatttaggt atgaaagcca gctacagatg gtacaggtga ccggctcctc agataatgag     60

tacttctacg ttgaaagcca gctacagatg gtacaggtga ccggctcctc agatagtgag    120

tacttctacg ttgatttcag agaatatgaa tatgatctca aatgggagtt tccaagagaa    180

aatttagagt ttggtaagaa tggaatgtgc caaatgtttc tgcagcattt cttttccatt    240

ggaaaatctt taaaatgcac gtactcacca tttgtctttg cagggaaggt actaggatca    300

ggtgcttttg gaaaagtgat gaacgcaaca gctttggaat tagcaaaaca ggagtctcaa    360

tccaggttgc cgtcaaaatg ctgaaa                                         386
```

```
<210> SEQ ID NO 12
<211> LENGTH: 480
<212> TYPE: DNA
<213> ORGANISM: Homo sapiens

<400> SEQUENCE: 12

caatttaggt atgaaagcca gctacagatg gtacaggtga ccggctcctc agataatgag     60

tacttctacg ttgatttcag agaatatgaa tatgatctca aatgggagtt tccaagagaa    120

aatttagagt ttggtaagaa tggaatgtgc caaatgtttc tgcagcattt cttttccatt    180

ggaaaatctt taaaatgcac gtactcacca tttgtctttg cagggaaggt actaggatcc    240

gaatatgatc tcaaatggga gtttccaaga gaaaatttag agtttggtga gaatggaatg    300

tgccaaatgt ttctgcagca tttcttttcc attggaaaat ctttaaaatg cacgtactca    360

ccatttgtct ttgcagggaa ggtactagga tcaggtgctt ttggaaaagt gatgaacgca    420

acagcttatg gaattagcaa aacaggagtc tcaatccagg ttgccgtcaa aatgctgaaa    480
```

```
<210> SEQ ID NO 13
<211> LENGTH: 366
<212> TYPE: DNA
<213> ORGANISM: Homo sapiens

<400> SEQUENCE: 13

caatttaggt atgaaagcca gctacagatg gtacaggtga ccggctcctc agataatgag     60

tacttctacg ttgatttcag agaatatgaa tatgatctca aatgggagtt tgatttcaga    120

gaatatgaat atgatctcaa atgggagttt ccaagagaaa atttagagtt tggtaagaat    180

ggaatgtgcc aaatgtttct gcagcatttc ttttccattg gaaaatcttt aaaatgcacg    240

tactcaccat ttgtctttgc agggaaggta ctaggatcag gtgcttttgg aaaagtgatg    300

aacgcaacag cttatggaat tagcaaaaca ggagtctcaa tccaggttgc cgtcaaaatg    360

ctgaaa                                                               366
```

```
<210> SEQ ID NO 14
<211> LENGTH: 357
<212> TYPE: DNA
<213> ORGANISM: Homo sapiens
```

<400> SEQUENCE: 14

```
caatttaggt atgaaagcca gctacagatg gtacaggtga ccggctcctc agataatgag     60

tacttctacg ttgatttcag agaatatgaa tatgatctca aatgggagtt tccaagagaa    120

aattggcaca aatgggagtt tccaagagaa aatttagagt ttggtaagaa tggaatgtgc    180

caaacgtttc tgcagcattt cttttccatt ggaaaatctt taaaatgcac gtactcacca    240

tttgtctttg cagggaaggt actaggatca ggtgcttttg gaaaagtgat gaacgcaaca    300

gcttatggaa ttagcaaaac aggagtctca atccaggttg ccgtcaaaat gctgaaa       357
```

<210> SEQ ID NO 15
<211> LENGTH: 366
<212> TYPE: DNA
<213> ORGANISM: Homo sapiens

<400> SEQUENCE: 15

```
caatttaggt atgaaagcca gctacagatg gtacaggtga ccggctcctc agataatgag     60

tacttctacg ttgatttcag aggctcctca gataatgagt acttctacgt tgatttcaga    120

gaatatgaat atgatctcaa atgggagttt ccaagagaaa atttagagtt tggtaagaat    180

ggaatgtgcc aaatgtttct gcagcatttc ttttccattg gaaaatcttt aaaatgcacg    240

tactcaccat ttgtctttgc agggaaggta ctaggatcag gtgcttttgg aaaagtgatg    300

aacgcaacag cttatggaat tagcaaaaca ggagtctcaa tccaggttgc cgtcaaaatg    360

ctgaaa                                                               366
```

<210> SEQ ID NO 16
<211> LENGTH: 665
<212> TYPE: PRT
<213> ORGANISM: Homo sapiens

<400> SEQUENCE: 16

```
Met Pro Ala Leu Ala Arg Asp Ala Gly Thr Val Pro Leu Leu Val Val
  1               5                  10                  15

Phe Ser Ala Met Ile Phe Gly Thr Ile Thr Asn Gln Asp Leu Pro Val
             20                  25                  30

Ile Lys Cys Val Leu Ile Asn His Lys Asn Asn Asp Ser Ser Val Gly
         35                  40                  45

Lys Ser Ser Ser Tyr Pro Met Val Ser Glu Ser Pro Glu Asp Leu Gly
     50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                 85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
    130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190
```

-continued

```
Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
    210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
        275                 280                 285

Asn Lys Ala Leu Glu Glu Gly Asn Tyr Phe Glu Met Ser Thr Tyr Ser
    290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Gly Lys Gly Phe Ile Asn Ala
            340                 345                 350

Thr Asn Ser Ser Glu Asp Tyr Glu Ile Asp Gln Tyr Glu Glu Phe Cys
        355                 360                 365

Phe Ser Val Arg Phe Lys Ala Tyr Pro Gln Ile Arg Cys Thr Trp Thr
    370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
            420                 425                 430

Leu Asn Ile Arg Arg Lys Pro Gln Val Leu Ala Glu Ala Ser Ala Ser
        435                 440                 445

Gln Ala Ser Cys Phe Ser Asp Gly Tyr Pro Leu Pro Ser Trp Thr Trp
    450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
    530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
            580                 585                 590

Glu Ser Gln Leu Gln Met Val Gln Val Thr Gly Ser Ser Asp Ser Glu
        595                 600                 605

Tyr Phe Tyr Val Asp Phe Arg Glu Tyr Glu Tyr Asp Leu Lys Trp Glu
    610                 615                 620
```

```
Phe Pro Arg Glu Asn Leu Glu Phe Gly Lys Val Leu Gly Ser Gly Ala
625                 630                 635                 640

Phe Gly Lys Val Met Asn Ala Thr Ala Leu Glu Leu Ala Lys Gln Glu
                645                 650                 655

Ser Gln Ser Arg Leu Pro Ser Lys Cys
            660                 665


<210> SEQ ID NO 17
<211> LENGTH: 994
<212> TYPE: PRT
<213> ORGANISM: Homo sapiens

<400> SEQUENCE: 17

Met Pro Ala Leu Ala Arg Asp Ala Gly Thr Val Pro Leu Leu Val Val
  1               5                  10                  15

Phe Ser Ala Met Ile Phe Gly Thr Ile Thr Asn Gln Asp Leu Pro Val
             20                  25                  30

Ile Lys Cys Val Leu Ile Asn His Lys Asn Asn Asp Ser Ser Val Gly
         35                  40                  45

Lys Ser Ser Ser Tyr Pro Met Val Ser Glu Ser Pro Glu Asp Leu Gly
     50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                 85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
    130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
    210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
        275                 280                 285

Asn Lys Ala Leu Glu Glu Gly Asn Tyr Phe Glu Met Ser Thr Tyr Ser
    290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335
```

```
Ser Gln Ser Ala Leu Val Thr Ile Val Gly Lys Gly Phe Ile Asn Ala
            340                 345                 350

Thr Asn Ser Ser Glu Asp Tyr Glu Ile Asp Gln Tyr Glu Glu Phe Cys
        355                 360                 365

Phe Ser Val Arg Phe Lys Ala Tyr Pro Gln Ile Arg Cys Thr Trp Thr
    370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
            420                 425                 430

Leu Asn Ile Arg Arg Lys Pro Gln Val Leu Ala Glu Ala Ser Ala Ser
        435                 440                 445

Gln Ala Ser Cys Phe Ser Asp Gly Tyr Pro Leu Pro Ser Trp Thr Trp
    450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
    530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
            580                 585                 590

Asp Phe Arg Glu Tyr Glu Tyr Asp Leu Lys Trp Glu Phe Pro Arg Glu
        595                 600                 605

Asn Leu Glu Phe Gly Lys Val Leu Gly Ser Glu Tyr Asp Leu Lys Trp
    610                 615                 620

Glu Phe Pro Arg Glu Asn Leu Glu Phe Gly Lys Val Leu Gly Ser Gly
625                 630                 635                 640

Ala Phe Gly Lys Val Met Asn Ala Thr Ala Tyr Gly Ile Ser Lys Thr
                645                 650                 655

Gly Val Ser Ile Gln Val Ala Val Lys Met Leu Lys Glu Lys Ala Asp
            660                 665                 670

Ser Ser Glu Arg Glu Ala Leu Met Ser Glu Leu Lys Met Met Thr Gln
        675                 680                 685

Leu Gly Ser His Glu Asn Ile Val Asn Leu Leu Gly Ala Cys Thr Leu
    690                 695                 700

Ser Gly Pro Ile Tyr Leu Ile Phe Glu Tyr Cys Cys Tyr Gly Asp Leu
705                 710                 715                 720

Leu Asn Tyr Leu Arg Ser Lys Arg Glu Lys Phe His Arg Thr Trp Thr
                725                 730                 735

Glu Ile Phe Lys Glu His Asn Phe Ser Phe Tyr Pro Thr Phe Gln Ser
            740                 745                 750

His Pro Asn Ser Ser Met Pro Gly Ser Arg Glu Val Gln Ile His Pro
        755                 760                 765
```

```
Asp Ser Asp Gln Ile Ser Gly Leu His Gly Asn Ser Phe His Ser Glu
    770                 775                 780

Asp Glu Ile Glu Tyr Glu Asn Gln Lys Arg Leu Glu Glu Glu Glu Asp
785                 790                 795                 800

Leu Asn Val Leu Thr Phe Glu Asp Leu Leu Cys Phe Ala Tyr Gln Val
                805                 810                 815

Ala Lys Gly Met Glu Phe Leu Glu Phe Lys Ser Cys Val His Arg Asp
            820                 825                 830

Leu Ala Ala Arg Asn Val Leu Val Thr His Gly Lys Val Val Lys Ile
        835                 840                 845

Cys Asp Phe Gly Leu Ala Arg Asp Ile Met Ser Asp Ser Asn Tyr Val
    850                 855                 860

Val Arg Gly Asn Ala Arg Leu Pro Val Lys Trp Met Ala Pro Glu Ser
865                 870                 875                 880

Leu Phe Glu Gly Ile Tyr Thr Ile Lys Ser Asp Val Trp Ser Tyr Gly
                885                 890                 895

Ile Leu Leu Trp Glu Ile Phe Ser Leu Gly Val Asn Pro Tyr Pro Gly
            900                 905                 910

Ile Pro Val Asp Ala Asn Phe Tyr Lys Leu Ile Gln Asn Gly Phe Lys
        915                 920                 925

Met Asp Gln Pro Phe Tyr Ala Thr Glu Glu Ile Tyr Ile Ile Met Gln
    930                 935                 940

Ser Cys Trp Ala Phe Asp Ser Arg Lys Arg Pro Ser Phe Pro Asn Leu
945                 950                 955                 960

Thr Ser Phe Leu Gly Cys Gln Leu Ala Asp Ala Glu Glu Ala Met Tyr
                965                 970                 975

Gln Asn Val Asp Gly Arg Val Ser Glu Cys Pro His Thr Tyr Gln Asn
            980                 985                 990

Arg Arg


<210> SEQ ID NO 18
<211> LENGTH: 986
<212> TYPE: PRT
<213> ORGANISM: Homo sapiens

<400> SEQUENCE: 18

Met Pro Ala Leu Ala Arg Asp Ala Gly Thr Val Pro Leu Leu Val Val
  1               5                  10                  15

Phe Ser Ala Met Ile Phe Gly Thr Ile Thr Asn Gln Asp Leu Pro Val
             20                  25                  30

Ile Lys Cys Val Leu Ile Asn His Lys Asn Asn Asp Ser Ser Val Gly
         35                  40                  45

Lys Ser Ser Ser Tyr Pro Met Val Ser Glu Ser Pro Glu Asp Leu Gly
     50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                 85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
    130                 135                 140
```

-continued

```
Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
    210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
        275                 280                 285

Asn Lys Ala Leu Glu Glu Gly Asn Tyr Phe Glu Met Ser Thr Tyr Ser
    290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Gly Lys Gly Phe Ile Asn Ala
            340                 345                 350

Thr Asn Ser Ser Glu Asp Tyr Glu Ile Asp Gln Tyr Glu Glu Phe Cys
        355                 360                 365

Phe Ser Val Arg Phe Lys Ala Tyr Pro Gln Ile Arg Cys Thr Trp Thr
    370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
            420                 425                 430

Leu Asn Ile Arg Arg Lys Pro Gln Val Leu Ala Glu Ala Ser Ala Ser
        435                 440                 445

Gln Ala Ser Cys Phe Ser Asp Gly Tyr Pro Leu Pro Ser Trp Thr Trp
    450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
    530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575
```

```
Gln Met Val Gln Val Thr Gly Ser Ser Asp Asn Glu Tyr Phe Tyr Val
            580                 585                 590

Asp Phe Arg Glu Tyr Glu Tyr Asp Leu Lys Trp Glu Phe Asp Phe Arg
        595                 600                 605

Glu Tyr Glu Tyr Asp Leu Lys Trp Glu Phe Pro Arg Glu Asn Leu Glu
    610                 615                 620

Phe Gly Lys Val Leu Gly Ser Gly Ala Phe Gly Lys Val Met Asn Ala
625                 630                 635                 640

Thr Ala Tyr Gly Ile Ser Lys Thr Gly Val Ser Ile Gln Val Ala Val
                645                 650                 655

Lys Met Leu Lys Glu Lys Ala Asp Ser Ser Glu Arg Glu Ala Leu Met
            660                 665                 670

Ser Glu Leu Lys Met Met Thr Gln Leu Gly Ser His Glu Asn Ile Val
        675                 680                 685

Asn Leu Leu Gly Ala Cys Thr Leu Ser Gly Pro Ile Tyr Leu Ile Phe
    690                 695                 700

Glu Tyr Cys Cys Tyr Gly Asp Leu Leu Asn Tyr Leu Arg Ser Lys Arg
705                 710                 715                 720

Glu Lys Phe His Arg Thr Trp Thr Glu Ile Phe Lys Glu His Asn Phe
                725                 730                 735

Ser Phe Tyr Pro Thr Phe Gln Ser His Pro Asn Ser Ser Met Pro Gly
            740                 745                 750

Ser Arg Glu Val Gln Ile His Pro Asp Ser Asp Gln Ile Ser Gly Leu
        755                 760                 765

His Gly Asn Ser Phe His Ser Glu Asp Glu Ile Glu Tyr Glu Asn Gln
    770                 775                 780

Lys Arg Leu Glu Glu Glu Glu Asp Leu Asn Val Leu Thr Phe Glu Asp
785                 790                 795                 800

Leu Leu Cys Phe Ala Tyr Gln Val Ala Lys Gly Met Glu Phe Leu Glu
                805                 810                 815

Phe Lys Ser Cys Val His Arg Asp Leu Ala Ala Arg Asn Val Leu Val
            820                 825                 830

Thr His Gly Lys Val Val Lys Ile Cys Asp Phe Gly Leu Ala Arg Asp
        835                 840                 845

Ile Met Ser Asp Ser Asn Tyr Val Val Arg Gly Asn Ala Arg Leu Pro
    850                 855                 860

Val Lys Trp Met Ala Pro Glu Ser Leu Phe Glu Gly Ile Tyr Thr Ile
865                 870                 875                 880

Lys Ser Asp Val Trp Ser Tyr Gly Ile Leu Leu Trp Glu Ile Phe Ser
                885                 890                 895

Leu Gly Val Asn Pro Tyr Pro Gly Ile Pro Val Asp Ala Asn Phe Tyr
            900                 905                 910

Lys Leu Ile Gln Asn Gly Phe Lys Met Asp Gln Pro Phe Tyr Ala Thr
        915                 920                 925

Glu Glu Ile Tyr Ile Ile Met Gln Ser Cys Trp Ala Phe Asp Ser Arg
    930                 935                 940

Lys Arg Pro Ser Phe Pro Asn Leu Thr Ser Phe Leu Gly Cys Gln Leu
945                 950                 955                 960

Ala Asp Ala Glu Glu Ala Met Tyr Gln Asn Val Asp Gly Arg Val Ser
                965                 970                 975

Glu Cys Pro His Thr Tyr Gln Asn Arg Arg
            980                 985
```

```
<210> SEQ ID NO 19
<211> LENGTH: 983
<212> TYPE: PRT
<213> ORGANISM: Homo sapiens

<400> SEQUENCE: 19

Met Pro Ala Leu Ala Arg Asp Ala Gly Thr Val Pro Leu Leu Val Val
  1               5                  10                  15

Phe Ser Ala Met Ile Phe Gly Thr Ile Thr Asn Gln Asp Leu Pro Val
             20                  25                  30

Ile Lys Cys Val Leu Ile Asn His Lys Asn Asn Asp Ser Ser Val Gly
         35                  40                  45

Lys Ser Ser Ser Tyr Pro Met Val Ser Glu Ser Pro Glu Asp Leu Gly
     50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                 85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
    130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
    210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
        275                 280                 285

Asn Lys Ala Leu Glu Glu Gly Asn Tyr Phe Glu Met Ser Thr Tyr Ser
    290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Gly Lys Gly Phe Ile Asn Ala
            340                 345                 350

Thr Asn Ser Ser Glu Asp Tyr Glu Ile Asp Gln Tyr Glu Glu Phe Cys
        355                 360                 365

Phe Ser Val Arg Phe Lys Ala Tyr Pro Gln Ile Arg Cys Thr Trp Thr
    370                 375                 380
```

```
Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
            420                 425                 430

Leu Asn Ile Arg Arg Lys Pro Gln Val Leu Ala Glu Ala Ser Ala Ser
        435                 440                 445

Gln Ala Ser Cys Phe Ser Asp Gly Tyr Pro Leu Pro Ser Trp Thr Trp
    450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
    530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
            580                 585                 590

Asp Phe Arg Glu Tyr Glu Tyr Asp Leu Lys Trp Glu Phe Pro Arg Glu
        595                 600                 605

Asn Trp His Lys Trp Glu Phe Pro Arg Glu Asn Leu Glu Phe Gly Lys
    610                 615                 620

Val Leu Gly Ser Gly Ala Phe Gly Lys Val Met Asn Ala Thr Ala Tyr
625                 630                 635                 640

Gly Ile Ser Lys Thr Gly Val Ser Ile Gln Val Ala Val Lys Met Leu
                645                 650                 655

Lys Glu Lys Ala Asp Ser Ser Glu Arg Glu Ala Leu Met Ser Glu Leu
            660                 665                 670

Lys Met Met Thr Gln Leu Gly Ser His Glu Asn Ile Val Asn Leu Leu
        675                 680                 685

Gly Ala Cys Thr Leu Ser Gly Pro Ile Tyr Leu Ile Phe Glu Tyr Cys
    690                 695                 700

Cys Tyr Gly Asp Leu Leu Asn Tyr Leu Arg Ser Lys Arg Glu Lys Phe
705                 710                 715                 720

His Arg Thr Trp Thr Glu Ile Phe Lys Glu His Asn Phe Ser Phe Tyr
                725                 730                 735

Pro Thr Phe Gln Ser His Pro Asn Ser Ser Met Pro Gly Ser Arg Glu
            740                 745                 750

Val Gln Ile His Pro Asp Ser Asp Gln Ile Ser Gly Leu His Gly Asn
        755                 760                 765

Ser Phe His Ser Glu Asp Glu Ile Glu Tyr Glu Asn Gln Lys Arg Leu
    770                 775                 780

Glu Glu Glu Glu Asp Leu Asn Val Leu Thr Phe Glu Asp Leu Leu Cys
785                 790                 795                 800

Phe Ala Tyr Gln Val Ala Lys Gly Met Glu Phe Leu Glu Phe Lys Ser
                805                 810                 815
```

```
Cys Val His Arg Asp Leu Ala Ala Arg Asn Val Leu Val Thr His Gly
            820                 825                 830

Lys Val Val Lys Ile Cys Asp Phe Gly Leu Ala Arg Asp Ile Met Ser
        835                 840                 845

Asp Ser Asn Tyr Val Val Arg Gly Asn Ala Arg Leu Pro Val Lys Trp
    850                 855                 860

Met Ala Pro Glu Ser Leu Phe Glu Gly Ile Tyr Thr Ile Lys Ser Asp
865                 870                 875                 880

Val Trp Ser Tyr Gly Ile Leu Leu Trp Glu Ile Phe Ser Leu Gly Val
                885                 890                 895

Asn Pro Tyr Pro Gly Ile Pro Val Asp Ala Asn Phe Tyr Lys Leu Ile
            900                 905                 910

Gln Asn Gly Phe Lys Met Asp Gln Pro Phe Tyr Ala Thr Glu Glu Ile
        915                 920                 925

Tyr Ile Ile Met Gln Ser Cys Trp Ala Phe Asp Ser Arg Lys Arg Pro
    930                 935                 940

Ser Phe Pro Asn Leu Thr Ser Phe Leu Gly Cys Gln Leu Ala Asp Ala
945                 950                 955                 960

Glu Glu Ala Met Tyr Gln Asn Val Asp Gly Arg Val Ser Glu Cys Pro
                965                 970                 975

His Thr Tyr Gln Asn Arg Arg
            980


<210> SEQ ID NO 20
<211> LENGTH: 986
<212> TYPE: PRT
<213> ORGANISM: Homo sapiens

<400> SEQUENCE: 20

Met Pro Ala Leu Ala Arg Asp Ala Gly Thr Val Pro Leu Leu Val Val
  1               5                  10                  15

Phe Ser Ala Met Ile Phe Gly Thr Ile Thr Asn Gln Asp Leu Pro Val
             20                  25                  30

Ile Lys Cys Val Leu Ile Asn His Lys Asn Asn Asp Ser Ser Val Gly
         35                  40                  45

Lys Ser Ser Ser Tyr Pro Met Val Ser Glu Ser Pro Glu Asp Leu Gly
     50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
    130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
        195                 200                 205
```

```
Glu Ser Pro Ala Val Val Lys Lys Glu Glu Lys Val Leu His Glu Leu
    210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
        275                 280                 285

Asn Lys Ala Leu Glu Glu Gly Asn Tyr Phe Glu Met Ser Thr Tyr Ser
    290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Gly Lys Gly Phe Ile Asn Ala
            340                 345                 350

Thr Asn Ser Ser Glu Asp Tyr Glu Ile Asp Gln Tyr Glu Glu Phe Cys
        355                 360                 365

Phe Ser Val Arg Phe Lys Ala Tyr Pro Gln Ile Arg Cys Thr Trp Thr
    370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
            420                 425                 430

Leu Asn Ile Arg Arg Lys Pro Gln Val Leu Ala Glu Ala Ser Ala Ser
        435                 440                 445

Gln Ala Ser Cys Phe Ser Asp Gly Tyr Pro Leu Pro Ser Trp Thr Trp
    450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
    530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
            580                 585                 590

Asp Phe Arg Gly Ser Ser Asp Asn Glu Tyr Phe Tyr Val Asp Phe Arg
        595                 600                 605

Glu Tyr Glu Tyr Asp Leu Lys Trp Glu Phe Pro Arg Glu Asn Leu Glu
    610                 615                 620

Phe Gly Lys Val Leu Gly Ser Gly Ala Phe Gly Lys Val Met Asn Ala
625                 630                 635                 640
```

```
Thr Ala Tyr Gly Ile Ser Lys Thr Gly Val Ser Ile Gln Val Ala Val
                645                 650                 655

Lys Met Leu Lys Glu Lys Ala Asp Ser Ser Glu Arg Glu Ala Leu Met
            660                 665                 670

Ser Glu Leu Lys Met Met Thr Gln Leu Gly Ser His Glu Asn Ile Val
        675                 680                 685

Asn Leu Leu Gly Ala Cys Thr Leu Ser Gly Pro Ile Tyr Leu Ile Phe
    690                 695                 700

Glu Tyr Cys Cys Tyr Gly Asp Leu Leu Asn Tyr Leu Arg Ser Lys Arg
705                 710                 715                 720

Glu Lys Phe His Arg Thr Trp Thr Glu Ile Phe Lys Glu His Asn Phe
                725                 730                 735

Ser Phe Tyr Pro Thr Phe Gln Ser His Pro Asn Ser Ser Met Pro Gly
            740                 745                 750

Ser Arg Glu Val Gln Ile His Pro Asp Ser Asp Gln Ile Ser Gly Leu
        755                 760                 765

His Gly Asn Ser Phe His Ser Glu Asp Glu Ile Glu Tyr Glu Asn Gln
    770                 775                 780

Lys Arg Leu Glu Glu Glu Glu Asp Leu Asn Val Leu Thr Phe Glu Asp
785                 790                 795                 800

Leu Leu Cys Phe Ala Tyr Gln Val Ala Lys Gly Met Glu Phe Leu Glu
                805                 810                 815

Phe Lys Ser Cys Val His Arg Asp Leu Ala Ala Arg Asn Val Leu Val
            820                 825                 830

Thr His Gly Lys Val Val Lys Ile Cys Asp Phe Gly Leu Ala Arg Asp
        835                 840                 845

Ile Met Ser Asp Ser Asn Tyr Val Val Arg Gly Asn Ala Arg Leu Pro
    850                 855                 860

Val Lys Trp Met Ala Pro Glu Ser Leu Phe Glu Gly Ile Tyr Thr Ile
865                 870                 875                 880

Lys Ser Asp Val Trp Ser Tyr Gly Ile Leu Leu Trp Glu Ile Phe Ser
                885                 890                 895

Leu Gly Val Asn Pro Tyr Pro Gly Ile Pro Val Asp Ala Asn Phe Tyr
            900                 905                 910

Lys Leu Ile Gln Asn Gly Phe Lys Met Asp Gln Pro Phe Tyr Ala Thr
        915                 920                 925

Glu Glu Ile Tyr Ile Ile Met Gln Ser Cys Trp Ala Phe Asp Ser Arg
    930                 935                 940

Lys Arg Pro Ser Phe Pro Asn Leu Thr Ser Phe Leu Gly Cys Gln Leu
945                 950                 955                 960

Ala Asp Ala Glu Glu Ala Met Tyr Gln Asn Val Asp Gly Arg Val Ser
                965                 970                 975

Glu Cys Pro His Thr Tyr Gln Asn Arg Arg
            980                 985
```

```
<210> SEQ ID NO 21
<211> LENGTH: 2978
<212> TYPE: DNA
<213> ORGANISM: Homo sapiens

<400> SEQUENCE: 21

atgccggcgt tggcgcgcga cgcgggcacc gtgccgctgc tcgttgtttt ttctgcaatg      60

atatttggga ctattacaaa tcaagatctg cctgtgatca agtgtgtttt aatcaatcat     120

aagaacaatg attcatcagt ggggaagtca tcatcatatc ccatggtatc agaatccccg     180
```

-continued

```
gaagacctcg ggtgtgcgtt gagaccccag agctcaggga cagtgtacga agctgccgct    240
gtggaagtgg atgtatctgc ttccatcaca ctgcaagtgc tggtcgatgc cccagggaac    300
atttcctgtc tctgggtctt taagcacagc tccctgaatt gccagccaca ttttgattta    360
caaaacagag gagttgtttc catggtcatt ttgaaaatga cagaaaccca agctggagaa    420
tacctacttt ttattcagag tgaagctacc aattacacaa tattgtttac agtgagtata    480
agaaataccc tgctttacac attaagaaga ccttacttta gaaaaatgga aaaccaggac    540
gccctggtct gcatatctga gagcgttcca gagccgatcg tggaatgggt gctttgcgat    600
tcacaggggg aaagctgtaa agaagaaagt ccagctgttg ttaaaaagga ggaaaaagtg    660
cttcatgaat tatttgggac ggacataagg tgctgtgcca gaaatgaact gggcagggaa    720
tgcaccaggc tgttcacaat agatctaaat caaactcctc agaccacatt gccacaatta    780
tttcttaaag taggggaacc cttatggata aggtgcaaag ctgttcatgt gaaccatgga    840
ttcgggctca cctgggaatt agaaaacaaa gcactcgagg agggcaacta ctttgagatg    900
agtacctatt caacaaacag aactatgata cggattctgt ttgcttttgt atcatcagtg    960
gcaagaaacg acaccggata ctacacttgt tcctcttcaa agcatcccag tcaatcagct   1020
ttggttacca tcgtaggaaa gggatttata aatgctacca attcaagtga agattatgaa   1080
attgaccaat atgaagagtt ttgtttttct gtcaggttta aagcctaccc acaaatcaga   1140
tgtacgtgga ccttctctcg aaaatcattt ccttgtgagc aaaagggtct tgataacgga   1200
tacagcatat ccaagttttg caatcataag caccagccag gagaatatat attccatgca   1260
gaaaatgatg atgcccaatt taccaaaatg ttcacgctga atataagaag gaaacctcaa   1320
gtgctcgcag aagcatcggc aagtcaggcg tcctgtttct cggatggata cccattacca   1380
tcttggacct ggaagaagtg ttcagacaag tctcccaact gcacagaaga gatcacagaa   1440
ggagtctgga atagaaaggc taacagaaaa gtgtttggac agtgggtgtc gagcagtact   1500
ctaaacatga gtgaagccat aaaagggttc ctggtcaagt gctgtgcata caattccctt   1560
ggcacatctt gtgagacgat ccttttaaac tctccaggcc ccttcccttt catccaagac   1620
aacatctcat tctatgcaac aattggtgtt tgtctcctct tcattgtcgt tttaaccctg   1680
ctaatttgtc acaagtacaa aaagcaattt aggtatgaaa gccagctaca gatggtacag   1740
gtgaccggct cctcagataa tgagtacttc tacgttgaaa gccagctaca gatggtacag   1800
gtgaccggct cctcagatag tgagtacttc tacgttgatt tcagagaata tgaatatgat   1860
ctcaaatggg agtttccaag agaaaattta gagtttggga aggtactagg atcaggtgct   1920
tttggaaaag tgatgaacgc aacagctttg gaattagcaa aacaggagtc tcaatccagg   1980
ttgccgtcaa aatgctgaaa gaaaaagcag acagctctga aagagaggca ctcatgtcag   2040
aactcaagat gatgacccag ctgggaagcc acgagaatat tgtgaacctg ctgggggcgt   2100
gcacactgtc aggaccaatt tacttgattt ttgaatactg ttgctatggt gatcttctca   2160
actatctaag aagtaaaaga gaaaaatttc acaggacttg gacagagatt ttcaaggaac   2220
acaatttcag tttttacccc actttccaat cacatccaaa ttccagcatg cctggttcaa   2280
gagaagttca gatacacccg gactcggatc aaatctcagg gcttcatggg aattcatttc   2340
actctgaaga tgaaattgaa tatgaaaacc aaaaaaggct ggaagaagag gaggacttga   2400
atgtgcttac atttgaagat cttctttgct ttgcatatca agttgccaaa ggaatggaat   2460
ttctggaatt taagtcgtgt gttcacagag acctggccgc caggaacgtg cttgtcaccc   2520
acgggaaagt ggtgaagata tgtgactttg gattggctcg agatatcatg agtgattcca   2580
```

```
actatgttgt caggggcaat gcccgtctgc ctgtaaaatg gatggccccc gaaagcctgt   2640

ttgaaggcat ctacaccatt aagagtgatg tctggtcata tggaatatta ctgtgggaaa   2700

tcttctcact tggtgtgaat ccttaccctg gcattccggt tgatgctaac ttctacaaac   2760

tgattcaaaa tggatttaaa atggatcagc cattttatgc tacagaagaa atatacatta   2820

taatgcaatc ctgctgggct tttgactcaa ggaaacggcc atccttccct aatttgactt   2880

cgtttttagg atgtcagctg gcagatgcag aagaagcgat gtatcagaat gtggatggcc   2940

gtgtttcgga atgtcctcac acctaccaaa acaggcga                           2978
```

<210> SEQ ID NO 22
<211> LENGTH: 2982
<212> TYPE: DNA
<213> ORGANISM: Homo sapiens

<400> SEQUENCE: 22

```
atgccggcgt tggcgcgcga cgcgggcacc gtgccgctgc tcgttgtttt ttctgcaatg     60

atatttggga ctattacaaa tcaagatctg cctgtgatca agtgtgtttt aatcaatcat    120

aagaacaatg attcatcagt ggggaagtca tcatcatatc ccatggtatc agaatccccg    180

gaagacctcg ggtgtgcgtt gagaccccag agctcaggga cagtgtacga agctgccgct    240

gtggaagtgg atgtatctgc ttccatcaca ctgcaagtgc tggtcgatgc cccagggaac    300

atttcctgtc tctgggtctt taagcacagc tccctgaatt gccagccaca ttttgattta    360

caaaacagag gagttgtttc catggtcatt ttgaaaatga cagaaaccca agctggagaa    420

tacctacttt ttattcagag tgaagctacc aattacacaa tattgtttac agtgagtata    480

agaaataccc tgctttacac attaagaaga ccttacttta gaaaaatgga aaaccaggac    540

gccctggtct gcatatctga gagcgttcca gagccgatcg tggaatgggt gctttgcgat    600

tcacaggggg aaagctgtaa agaagaaagt ccagctgttg ttaaaaagga ggaaaaagtg    660

cttcatgaat tatttgggac ggacataagg tgctgtgcca gaaatgaact gggcagggaa    720

tgcaccaggc tgttcacaat agatctaaat caaactcctc agaccacatt gccacaatta    780

tttcttaaag taggggaacc cttatggata aggtgcaaag ctgttcatgt gaaccatgga    840

ttcgggctca cctgggaatt agaaaacaaa gcactcgagg agggcaacta ctttgagatg    900

agtacctatt caacaaacag aactatgata cggattctgt ttgcttttgt atcatcagtg    960

gcaagaaacg acaccggata ctacacttgt tcctcttcaa agcatcccag tcaatcagct   1020

ttggttacca tcgtaggaaa gggatttata aatgctacca attcaagtga agattatgaa   1080

attgaccaat atgaagagtt ttgtttttct gtcaggttta aagcctaccc acaaatcaga   1140

tgtacgtgga ccttctctcg aaaatcattt ccttgtgagc aaaagggtct tgataacgga   1200

tacagcatat ccaagttttg caatcataag caccagccag gagaatatat attccatgca   1260

gaaaatgatg atgcccaatt taccaaaatg ttcacgctga atataagaag gaaacctcaa   1320

gtgctcgcag aagcatcggc aagtcaggcg tcctgtttct cggatggata cccattacca   1380

tcttggacct ggaagaagtg ttcagacaag tctcccaact gcacagaaga gatcacagaa   1440

ggagtctgga atagaaaggc taacagaaaa gtgtttggac agtgggtgtc gagcagtact   1500

ctaaacatga gtgaagccat aaaagggttc ctggtcaagt gctgtgcata caattccctt   1560

ggcacatctt gtgagacgat ccttttaaac tctccaggcc ccttcccttt catccaagac   1620

aacatctcat tctatgcaac aattggtgtt tgtctcctct tcattgtcgt tttaaccctg   1680

ctaatttgtc acaagtacaa aaagcaattt aggtatgaaa gccagctaca gatggtacag   1740
```

```
gtgaccggct cctcagataa tgagtacttc tacgttgatt tcagagaata tgaatatgat   1800

ctcaaatggg agtttccaag agaaaattta gagtttggga aggtactagg atccgaatat   1860

gatctcaaat gggagtttcc aagagaaaat ttagagtttg ggaaggtact aggatcaggt   1920

gcttttggaa aagtgatgaa cgcaacagct tatggaatta gcaaaacagg agtctcaatc   1980

caggttgccg tcaaaatgct gaaagaaaaa gcagacagct ctgaaagaga ggcactcatg   2040

tcagaactca agatgatgac ccagctggga agccacgaga atattgtgaa cctgctgggg   2100

gcgtgcacac tgtcaggacc aatttacttg atttttgaat actgttgcta tggtgatctt   2160

ctcaactatc taagaagtaa aagagaaaaa tttcacagga cttggacaga gattttcaag   2220

gaacacaatt tcagttttta ccccactttc caatcacatc caaattccag catgcctggt   2280

tcaagagaag ttcagataca cccggactcg gatcaaatct cagggcttca tgggaattca   2340

tttcactctg aagatgaaat tgaatatgaa aaccaaaaaa ggctggaaga agaggaggac   2400

ttgaatgtgc ttacatttga agatcttctt tgctttgcat atcaagttgc caaaggaatg   2460

gaatttctgg aatttaagtc gtgtgttcac agagacctgg ccgccaggaa cgtgcttgtc   2520

acccacggga aagtggtgaa gatatgtgac tttggattgg ctcgagatat catgagtgat   2580

tccaactatg ttgtcagggg caatgcccgt ctgcctgtaa aatggatggc cccgaaagc    2640

ctgtttgaag gcatctacac cattaagagt gatgtctggt catatggaat attactgtgg   2700

gaaatcttct cacttggtgt gaatccttac cctggcattc cggttgatgc taacttctac   2760

aaactgattc aaaatggatt taaaatggat cagccatttt atgctacaga agaaatatac   2820

attataatgc aatcctgctg ggcttttgac tcaaggaaac ggccatcctt ccctaatttg   2880

acttcgtttt taggatgtca gctggcagat gcagaagaag cgatgtatca gaatgtggat   2940

ggccgtgttt cggaatgtcc tcacacctac caaaacaggc ga                      2982
```

<210> SEQ ID NO 23
<211> LENGTH: 2958
<212> TYPE: DNA
<213> ORGANISM: Homo sapiens

<400> SEQUENCE: 23

```
atgccggcgt tggcgcgcga cgcgggcacc gtgccgctgc tcgttgtttt ttctgcaatg     60

atatttggga ctattacaaa tcaagatctg cctgtgatca agtgtgtttt aatcaatcat    120

aagaacaatg attcatcagt ggggaagtca tcatcatatc ccatggtatc agaatccccg    180

gaagacctcg ggtgtgcgtt gagaccccag agctcaggga cagtgtacga agctgccgct    240

gtggaagtgg atgtatctgc ttccatcaca ctgcaagtgc tggtcgatgc cccagggaac    300

atttcctgtc tctgggtctt taagcacagc tccctgaatt gccagccaca ttttgattta    360

caaaacagag gagttgtttc catggtcatt ttgaaaatga cagaaaccca agctggagaa    420

tacctacttt ttattcagag tgaagctacc aattacacaa tattgtttac agtgagtata    480

agaaataccc tgctttacac attaagaaga ccttacttta gaaaaatgga aaaccaggac    540

gccctggtct gcatatctga gagcgttcca gagccgatcg tggaatgggt gctttgcgat    600

tcacaggggg aaagctgtaa agaagaaagt ccagctgttg ttaaaaagga ggaaaaagtg    660

cttcatgaat tatttgggac ggacataagg tgctgtgcca gaaatgaact gggcagggaa    720

tgcaccaggc tgttcacaat agatctaaat caaactcctc agaccacatt gccacaatta    780

tttcttaaag taggggaacc cttatggata aggtgcaaag ctgttcatgt gaaccatgga    840
```

```
ttcgggctca cctgggaatt agaaaacaaa gcactcgagg agggcaacta ctttgagatg    900

agtacctatt caacaaacag aactatgata cggattctgt ttgcttttgt atcatcagtg    960

gcaagaaacg acaccggata ctacacttgt tcctcttcaa agcatcccag tcaatcagct   1020

ttggttacca tcgtaggaaa gggatttata aatgctacca attcaagtga agattatgaa   1080

attgaccaat atgaagagtt ttgtttttct gtcaggttta aagcctaccc acaaatcaga   1140

tgtacgtgga ccttctctcg aaaatcattt ccttgtgagc aaaagggtct tgataacgga   1200

tacagcatat ccaagttttg caatcataag caccagccag gagaatatat attccatgca   1260

gaaaatgatg atgcccaatt taccaaaatg ttcacgctga atataagaag gaaacctcaa   1320

gtgctcgcag aagcatcggc aagtcaggcg tcctgtttct cggatggata cccattacca   1380

tcttggacct ggaagaagtg ttcagacaag tctcccaact gcacagaaga gatcacagaa   1440

ggagtctgga atagaaaggc taacagaaaa gtgtttggac agtgggtgtc gagcagtact   1500

ctaaacatga gtgaagccat aaaagggttc ctggtcaagt gctgtgcata caattccctt   1560

ggcacatctt gtgagacgat ccttttaaac tctccaggcc ccttcccttt catccaagac   1620

aacatctcat tctatgcaac aattggtgtt tgtctcctct tcattgtcgt tttaaccctg   1680

ctaatttgtc acaagtacaa aaagcaattt aggtatgaaa gccagctaca gatggtacag   1740

gtgaccggct cctcagataa tgagtacttc tacgttgatt tcagagaata tgaatatgat   1800

ctcaaatggg agtttgattt cagagaatat gaatatgatc tcaaatggga gtttccaaga   1860

gaaaatttag agtttgggaa ggtactagga tcaggtgctt ttggaaaagt gatgaacgca   1920

acagcttatg gaattagcaa aacaggagtc tcaatccagg ttgccgtcaa aatgctgaaa   1980

gaaaaagcag acagctctga aagagaggca ctcatgtcag aactcaagat gatgacccag   2040

ctgggaagcc acgagaatat tgtgaacctg ctgggggcgt gcacactgtc aggaccaatt   2100

tacttgattt ttgaatactg ttgctatggt gatcttctca actatctaag aagtaaaaga   2160

gaaaaatttc acaggacttg gacagagatt ttcaaggaac acaatttcag tttttacccc   2220

actttccaat cacatccaaa ttccagcatg cctggttcaa gagaagttca gatacacccg   2280

gactcggatc aaatctcagg gcttcatggg aattcatttc actctgaaga tgaaattgaa   2340

tatgaaaacc aaaaaaggct ggaagaagag gaggacttga atgtgcttac atttgaagat   2400

cttctttgct ttgcatatca agttgccaaa ggaatggaat ttctggaatt taagtcgtgt   2460

gttcacagag acctggccgc caggaacgtg cttgtcaccc acgggaaagt ggtgaagata   2520

tgtgactttg gattggctcg agatatcatg agtgattcca actatgttgt caggggcaat   2580

gcccgtctgc ctgtaaaatg gatggccccc gaaagcctgt ttgaaggcat ctacaccatt   2640

aagagtgatg tctggtcata tggaatatta ctgtgggaaa tcttctcact tggtgtgaat   2700

ccttaccctg gcattccggt tgatgctaac ttctacaaac tgattcaaaa tggatttaaa   2760

atggatcagc cattttatgc tacagaagaa atatacatta taatgcaatc ctgctgggct   2820

tttgactcaa ggaaacggcc atccttccct aatttgactt cgtttttagg atgtcagctg   2880

gcagatgcag aagaagcgat gtatcagaat gtggatggcc gtgtttcgga atgtcctcac   2940

acctaccaaa acaggcga                                                 2958
```

<210> SEQ ID NO 24
<211> LENGTH: 2949
<212> TYPE: DNA
<213> ORGANISM: Homo sapiens

<400> SEQUENCE: 24

```
atgccggcgt tggcgcgcga cgcgggcacc gtgccgctgc tcgttgtttt ttctgcaatg     60
atatttggga ctattacaaa tcaagatctg cctgtgatca agtgtgtttt aatcaatcat    120
aagaacaatg attcatcagt ggggaagtca tcatcatatc ccatggtatc agaatccccg    180
gaagacctcg ggtgtgcgtt gagaccccag agctcaggga cagtgtacga agctgccgct    240
gtggaagtgg atgtatctgc ttccatcaca ctgcaagtgc tggtcgatgc cccagggaac    300
atttcctgtc tctgggtctt taagcacagc tccctgaatt gccagccaca ttttgattta    360
caaaacagag gagttgtttc catggtcatt ttgaaaatga cagaaaccca agctggagaa    420
tacctacttt ttattcagag tgaagctacc aattacacaa tattgtttac agtgagtata    480
agaaataccc tgctttacac attaagaaga ccttacttta gaaaaatgga aaaccaggac    540
gccctggtct gcatatctga gagcgttcca gagccgatcg tggaatgggt gctttgcgat    600
tcacaggggg aaagctgtaa agaagaaagt ccagctgttg ttaaaaagga ggaaaaagtg    660
cttcatgaat tatttgggac ggacataagg tgctgtgcca gaaatgaact gggcagggaa    720
tgcaccaggc tgttcacaat agatctaaat caaactcctc agaccacatt gccacaatta    780
tttcttaaag taggggaacc cttatggata aggtgcaaag ctgttcatgt gaaccatgga    840
ttcgggctca cctgggaatt agaaaacaaa gcactcgagg agggcaacta ctttgagatg    900
agtaccta tt caacaaacag aactatgata cggattctgt ttgcttttgt atcatcagtg    960
gcaagaaacg acaccggata ctacacttgt tcctcttcaa agcatcccag tcaatcagct   1020
ttggttacca tcgtaggaaa gggatttata aatgctacca attcaagtga agattatgaa   1080
attgaccaat atgaagagtt ttgtttttct gtcaggttta aagcctaccc acaaatcaga   1140
tgtacgtgga ccttctctcg aaaatcattt ccttgtgagc aaaagggtct tgataacgga   1200
tacagcatat ccaagttttg caatcataag caccagccag gagaatatat attccatgca   1260
gaaaatgatg atgcccaatt taccaaaatg ttcacgctga atataagaag gaaacctcaa   1320
gtgctcgcag aagcatcggc aagtcaggcg tcctgtttct cggatggata cccattacca   1380
tcttggacct ggaagaagtg ttcagacaag tctcccaact gcacagaaga gatcacagaa   1440
ggagtctgga atagaaaggc taacagaaaa gtgtttggac agtgggtgtc gagcagtact   1500
ctaaacatga gtgaagccat aaaagggttc ctggtcaagt gctgtgcata caattccctt   1560
ggcacatctt gtgagacgat ccttttaaac tctccaggcc ccttcccttt catccaagac   1620
aacatctcat tctatgcaac aattggtgtt tgtctcctct tcattgtcgt tttaaccctg   1680
ctaatttgtc acaagtacaa aaagcaattt aggtatgaaa gccagctaca gatggtacag   1740
gtgaccggct cctcagataa tgagtacttc tacgttgatt tcagagaata tgaatatgat   1800
ctcaaatggg agtttccaag agaaaattgg cacaaatggg agtttccaag agaaaattta   1860
gagtttggga aggtactagg atcaggtgct tttggaaaag tgatgaacgc aacagcttat   1920
ggaattagca aaacaggagt ctcaatccag gttgccgtca aaatgctgaa agaaaaagca   1980
gacagctctg aaagagaggc actcatgtca gaactcaaga tgatgaccca gctgggaagc   2040
cacgagaata ttgtgaacct gctgggggcg tgcacactgt caggaccaat ttacttgatt   2100
tttgaatact gttgctatgg tgatcttctc aactatctaa gaagtaaaag agaaaaattt   2160
cacaggactt ggacagagat tttcaaggaa cacaatttca gtttttaccc cactttccaa   2220
tcacatccaa attccagcat gcctggttca agagaagttc agatacaccc ggactcggat   2280
caaatctcag ggcttcatgg gaattcattt cactctgaag atgaaattga atatgaaaac   2340
```

```
caaaaaaggc tggaagaaga ggaggacttg aatgtgctta catttgaaga tcttctttgc   2400

tttgcatatc aagttgccaa aggaatggaa tttctggaat ttaagtcgtg tgttcacaga   2460

gacctggccg ccaggaacgt gcttgtcacc cacgggaaag tggtgaagat atgtgacttt   2520

ggattggctc gagatatcat gagtgattcc aactatgttg tcaggggcaa tgcccgtctg   2580

cctgtaaaat ggatggcccc cgaaagcctg tttgaaggca tctacaccat taagagtgat   2640

gtctggtcat atggaatatt actgtgggaa atcttctcac ttggtgtgaa tccttaccct   2700

ggcattccgg ttgatgctaa cttctacaaa ctgattcaaa atggatttaa aatggatcag   2760

ccattttatg ctacagaaga aatatacatt ataatgcaat cctgctgggc ttttgactca   2820

aggaaacggc catccttccc taatttgact tcgtttttag gatgtcagct ggcagatgca   2880

gaagaagcga tgtatcagaa tgtggatggc cgtgtttcgg aatgtcctca cacctaccaa   2940

aacaggcga                                                           2949
```

<210> SEQ ID NO 25
<211> LENGTH: 2958
<212> TYPE: DNA
<213> ORGANISM: Homo sapiens

<400> SEQUENCE: 25

```
atgccggcgt tggcgcgcga cgcgggcacc gtgccgctgc tcgttgtttt ttctgcaatg     60

atatttggga ctattacaaa tcaagatctg cctgtgatca agtgtgtttt aatcaatcat    120

aagaacaatg attcatcagt ggggaagtca tcatcatatc ccatggtatc agaatccccg    180

gaagacctcg ggtgtgcgtt gagaccccag agctcaggga cagtgtacga agctgccgct    240

gtggaagtgg atgtatctgc ttccatcaca ctgcaagtgc tggtcgatgc cccagggaac    300

atttcctgtc tctgggtctt taagcacagc tccctgaatt gccagccaca ttttgattta    360

caaaacagag gagttgtttc catggtcatt ttgaaaatga cagaaaccca agctggagaa    420

tacctacttt ttattcagag tgaagctacc aattacacaa tattgtttac agtgagtata    480

agaaataccc tgctttacac attaagaaga ccttacttta gaaaaatgga aaaccaggac    540

gccctggtct gcatatctga gagcgttcca gagccgatcg tggaatgggt gctttgcgat    600

tcacaggggg aaagctgtaa agaagaaagt ccagctgttg ttaaaaagga ggaaaaagtg    660

cttcatgaat tatttgggac ggacataagg tgctgtgcca gaaatgaact gggcagggaa    720

tgcaccaggc tgttcacaat agatctaaat caaactcctc agaccacatt gccacaatta    780

tttcttaaag taggggaacc cttatggata aggtgcaaag ctgttcatgt gaaccatgga    840

ttcgggctca cctgggaatt agaaaacaaa gcactcgagg agggcaacta ctttgagatg    900

agtacctatt caacaaacag aactatgata cggattctgt ttgcttttgt atcatcagtg    960

gcaagaaacg acaccggata ctacacttgt tcctcttcaa agcatcccag tcaatcagct   1020

ttggttacca tcgtaggaaa gggatttata aatgctacca attcaagtga agattatgaa   1080

attgaccaat atgaagagtt ttgtttttct gtcaggttta aagcctaccc acaaatcaga   1140

tgtacgtgga ccttctctcg aaaatcattt ccttgtgagc aaaagggtct tgataacgga   1200

tacagcatat ccaagttttg caatcataag caccagccag gagaatatat attccatgca   1260

gaaaatgatg atgcccaatt taccaaaatg ttcacgctga atataagaag gaaacctcaa   1320

gtgctcgcag aagcatcggc aagtcaggcg tcctgtttct cggatggata cccattacca   1380

tcttggacct ggaagaagtg ttcagacaag tctcccaact gcacagaaga gatcacagaa   1440
```

```
ggagtctgga atagaaaggc taacagaaaa gtgtttggac agtgggtgtc gagcagtact   1500

ctaaacatga gtgaagccat aaaagggttc ctggtcaagt gctgtgcata caattccctt   1560

ggcacatctt gtgagacgat ccttttaaac tctccaggcc ccttcccttt catccaagac   1620

aacatctcat tctatgcaac aattggtgtt tgtctcctct tcattgtcgt tttaaccctg   1680

ctaatttgtc acaagtacaa aaagcaattt aggtatgaaa gccagctaca gatggtacag   1740

gtgaccggct cctcagataa tgagtacttc tacgttgatt tcagaggctc ctcagataat   1800

gagtacttct acgttgattt cagagaatat gaatatgatc tcaaatggga gtttccaaga   1860

gaaaatttag agtttgggaa ggtactagga tcaggtgctt ttggaaaagt gatgaacgca   1920

acagcttatg gaattagcaa aacaggagtc tcaatccagg ttgccgtcaa aatgctgaaa   1980

gaaaaagcag acagctctga aagagaggca ctcatgtcag aactcaagat gatgacccag   2040

ctgggaagcc acgagaatat tgtgaacctg ctgggggcgt gcacactgtc aggaccaatt   2100

tacttgattt ttgaatactg ttgctatggt gatcttctca actatctaag aagtaaaaga   2160

gaaaaatttc acaggacttg gacagagatt ttcaaggaac acaatttcag tttttacccc   2220

actttccaat cacatccaaa ttccagcatg cctggttcaa gagaagttca gatacacccg   2280

gactcggatc aaatctcagg gcttcatggg aattcatttc actctgaaga tgaaattgaa   2340

tatgaaaacc aaaaaaggct ggaagaagag gaggacttga atgtgcttac atttgaagat   2400

cttctttgct ttgcatatca agttgccaaa ggaatggaat ttctggaatt taagtcgtgt   2460

gttcacagag acctggccgc caggaacgtg cttgtcaccc acgggaaagt ggtgaagata   2520

tgtgactttg gattggctcg agatatcatg agtgattcca actatgttgt caggggcaat   2580

gcccgtctgc ctgtaaaatg gatggccccc gaaagcctgt ttgaaggcat ctacaccatt   2640

aagagtgatg tctggtcata tggaatatta ctgtgggaaa tcttctcact tggtgtgaat   2700

ccttaccctg gcattccggt tgatgctaac ttctacaaac tgattcaaaa tggatttaaa   2760

atggatcagc cattttatgc tacagaagaa atatacatta taatgcaatc ctgctgggct   2820

tttgactcaa ggaaacggcc atccttccct aatttgactt cgtttttagg atgtcagctg   2880

gcagatgcag aagaagcgat gtatcagaat gtggatggcc gtgtttcgga atgtcctcac   2940

acctaccaaa acaggcga                                                 2958
```

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic DNA

<400> SEQUENCE: 26

```
tgtcgagcag tactctaaac a                                             21
```

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic DNA

<400> SEQUENCE: 27

```
atcctagtac cttcccaaac tc                                            22
```

```
<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28

cttcctgggc atggagtc                                                   18


<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29

cgctcaggag gagcaatgat                                                 20


<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30

caatttaggt atgaaagcc                                                  19


<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31

caaactctaa attttctct                                                  19


<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32

tgtctttgca gggaaggtta c                                               21


<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33

gtacctttca gcattttgac                                                 20
```